(12) United States Patent
Srivastava et al.

(10) Patent No.: US 8,877,204 B2
(45) Date of Patent: Nov. 4, 2014

(54) METHODS AND COMPOSITIONS FOR THE TREATMENT OF CANCER AND INFECTIOUS DISEASE USING ALPHA (2) MACROGLOBULIN-ANTIGENIC MOLECULE COMPLEXES

(75) Inventors: Pramod K. Srivastava, Avon, CT (US); Robert J. Binder, Farmington, CT (US)

(73) Assignee: University of Connecticut Health Center, Farmington, CT (US)

( * ) Notice: Subject to any disclaimer, the term of this patent is extended or adjusted under 35 U.S.C. 154(b) by 195 days.

(21) Appl. No.: 10/546,106

(22) PCT Filed: Feb. 20, 2004

(86) PCT No.: PCT/US2004/005110
§ 371 (c)(1),
(2), (4) Date: Oct. 11, 2005

(87) PCT Pub. No.: WO2004/074454
PCT Pub. Date: Sep. 2, 2004

(65) Prior Publication Data
US 2006/0165710 A1  Jul. 27, 2006

Related U.S. Application Data

(60) Provisional application No. 60/449,022, filed on Feb. 20, 2003, provisional application No. 60/450,751, filed on Feb. 27, 2003.

(51) Int. Cl.
*A61K 38/00* (2006.01)
*A61K 39/00* (2006.01)
*A61K 38/57* (2006.01)
*A61K 38/17* (2006.01)

(52) U.S. Cl.
CPC .............. *A61K 38/57* (2013.01); *A61K 39/0011* (2013.01); *A61K 38/1709* (2013.01); *A61K 2039/6031* (2013.01); *A61K 2039/605* (2013.01)
USPC ................ 424/185.1; 424/193.1; 424/196.11; 424/197.11; 424/195.11

(58) Field of Classification Search
None
See application file for complete search history.

(56) References Cited

U.S. PATENT DOCUMENTS

| | | | |
|---|---|---|---|
| 5,747,332 A | 5/1998 | Wallen et al. | |
| 5,750,119 A | 5/1998 | Srivastava | |
| 5,837,251 A | 11/1998 | Srivastava | |
| 5,948,646 A | 9/1999 | Srivastava et al. | |
| 5,985,270 A | 11/1999 | Srivastava | |
| 6,030,618 A | 2/2000 | Srivastava | |
| 6,156,311 A | 12/2000 | Strickland et al. | |
| 6,403,092 B1 | 6/2002 | Pizzo et al. | |
| 6,984,389 B2 * | 1/2006 | Li | 424/277.1 |
| 7,449,557 B2 | 11/2008 | Srivastava | |
| 2002/0028207 A1 | 3/2002 | Srivastava | |
| 2002/0192230 A1 | 12/2002 | Srivastava | |
| 2003/0129196 A1 | 7/2003 | Srivastava | |
| 2004/0022796 A1 | 2/2004 | Srivastava | |
| 2011/0318300 A1 | 12/2011 | Bachmann et al. | |

FOREIGN PATENT DOCUMENTS

| | | |
|---|---|---|
| JP | 2001/525347 | 12/2001 |
| JP | 2011/513369 | 4/2011 |
| WO | WO 94/14976 | 7/1994 |
| WO | WO 95/24923 | 9/1995 |
| WO | WO 96/10411 | 4/1996 |
| WO | WO 97/04794 | 2/1997 |
| WO | WO 97/10000 | 3/1997 |
| WO | WO 97/10001 | 3/1997 |
| WO | WO 97/10002 | 3/1997 |
| WO | WO 99/29182 | 6/1999 |
| WO | WO 01/91787 | 12/2001 |
| WO | WO 01/92474 | 12/2001 |
| WO | WO 02/32923 | 4/2002 |
| WO | WO 03/015712 | 2/2003 |
| WO | WO 2004/035602 | 4/2004 |
| WO | WO 2004/074454 | 9/2004 |
| WO | WO 2004/075636 | 9/2004 |
| WO | WO 2004/078921 | 9/2004 |
| WO | WO 2005/120558 | 12/2005 |

OTHER PUBLICATIONS

Bodey et al. (Anticancer Research, Jul.-Aug. 2000, vol. 20, pp. 2665-2676). Abstract only.*
Fields et al. (J. Virol. Methods vol. 22, pp. 283-294, 1988).*
Espana et al. (Clinical Chemistry vol. 42(4), p. 545-550 1996).*
Fundamental Immunology, by: William E. Paul, Third Edition, Raven Press, NY, 1993.*
Apantaku et al. (Breast cancer diagnosis and screening, American Family Physician, 62(3):596-602, 605-6, Aug. 2000).*
Martin et al (Journal of the National Cancer Institute, 92:1126-1135).*

(Continued)

*Primary Examiner* — Misook Yu
*Assistant Examiner* — Julie Wu
(74) *Attorney, Agent, or Firm* — Wolf, Greenfield & Sacks, P.C.

(57) ABSTRACT

The present invention relates to the use of alpha (2) macroglobulin complexes isolated from the serum of a mammal. The invention also relates to methods for making such complexes and compositions comprising alpha (2) macroglobulin complexes, isolated from the serum of a mammal, wherein such compositions are used in methods for the treatment and prevention of cancer and infectious disease. The invention also relates to methods for treating and preventing cancer and infectious disease using such complexes comprising, isolated from the serum of a mammal. The invention also encompasses methods for production of alpha (2) macroglobulin complexes.

15 Claims, 2 Drawing Sheets

(56) References Cited

OTHER PUBLICATIONS

Heeb et al., 1995, "Prostate specific antigen-alpha 2-macroglobulin complexes in prostate cancer patient sera," Biochem. Mol. Biol. Int. 37(5):917-23.
Koo, 1982, "Characterization of growth-inhibitory activities associated with an alpha-macroglobulin of mice," Cancer Res. 42(5):1788-97.
Stenman et al., 1991, "A complex between prostate-specific antigen and alpha 1-antichymotrypsin is the major form of prostate-specific antigen in serum of patients with prostatic cancer: assay of the complex improves clinical sensitivity for cancer," Cancer Res. 51(1):222-6.
Twining et al., 1977, "Large scale separation of protease inhibitors from malignant human breast tissue," Mol. Cell. Biochem. 18(2-3):101-7.
Office Action dated Jan. 30, 2003 in file history of U.S. Appl. No. 09/873,403.
Office Action dated Nov. 5, 2003 in file history of U.S. Appl. No. 09/873,403.
Office Action dated Nov. 17, 2004 in file history of U.S. Appl. No. 09/873,403.
Office Action dated Jun. 14, 2005 in file history of U.S. Appl. No. 09/873,403.
Office Action dated Mar. 13, 2006 in file history of U.S. Appl. No. 09/873,403.
Office Action dated Nov. 3, 2006 in file history of U.S. Appl. No. 09/873,403.
Office Action dated Apr. 17, 2007 in file history of U.S. Appl. No. 09/873,403.
Fields et al. Purity, antigenicity and immunogenicity of the hepatitis B surface antigen purified by five different methods. J Virol Methods. Dec. 1988;22(2-3):283-94.
Gura, T. Systems for identifying new drugs are often faulty. Science. Nov. 7, 1997;278(5340):1041-2.
Beyrer, C. The HIV/AIDS vaccine research effort: An update. The Hopkins HIV Report. Jan. 2003, 15(1): 6-7.
Anderson, 1994, "Effective Vaccination of Mice against Mycobacterium Tuberculosis Infection With a Soluble Mixture of Secreted Microbacterial Proteins." Infection Imm. 62:2536-2544.
Arnold et al., 1995, "Cross-priming of minor histocompatibility antigen-specific cytotoxic T cells upon immunization with the heat shock protein gp96." J. Exp. Med. 182:885-889.
Arnold-Schild et al., 1999, "Cutting edge: receptor-mediated endocytosis of heat shock proteins by professional antigen-presenting cells." J. Immunol. 162:3757-3760.
Bardwell et al., 1984, "Major heat shock gene of Drosophila and the *Escherichia coli* heat-inducible dnaK gene are homologous." Proc. Natl. Acad. Sci. USA 81:848-852.
Basu et al., 2000, "Necrotic but not apoptotic cell death releases heat shock proteins, which deliver a partial maturation signal to dendritic cells and activate the NF-kappa B pathway." Intl. Immunol 12(11):1539-1546.
Basu et al., 2001, "CD91 is a common receptor for heat shock proteins gp96, hsp90, hsp70, and calreticulin." Immunity 14(3):303-313.
Binder et al., 2000, "CD91: a receptor for heat shock protein gp96." Nature Immunol. 1:151-155.
Binder et al., 2000, "Saturation, competition, and specificity in interaction of heat shock proteins (hsp) gp96, hsp90, and hsp70 with CD11b+ cells." J. Immunol. 165:2582-2587.
Binder et al., 2001, "Adjuvanticity of $\alpha_2$—Macroglobulin, an Independent Ligand for the Heat Shock Protein Receptor CD91." J. Immunol. 166:4698-4972.
Binder et al., 2002, "Immuno-prophylaxis of tumors with non-covalent alpha2-macroglobulin-peptide complexes is CD91 dependent." 93rd Annual Meeting of American Association for Cancer Research Abs #2206.
Binder et al., 2002, "Naturally formed or artificially reconstituted non-covalent alpha2-macroglobulin peptide complexes elicit CD91-dependent cellular immunity." Cancer Immunity 2:16.
Bizik et al., 1986, "Human Tumor Cells Synthesize and Secrete Alpha-2 Macroglobulin In Vitro." Int. J. Cancer 37:81-88.
Blachere et al., 1997, "Heat shock protein-peptide complexes, reconstituted in vitro, elicit peptide-specific cytotoxic T lymphocyte response and tumor immunity." J. Exp. Med. 186:1315-22.
Breloer et al., 1998, "Isolation of processed, H-2Kb-binding ovalbumin-derived peptides associated with the stress proteins HSP70 and gp96." Eur. J. Immunol. 28:1016-1021.
Chu & Pizzo, 1993, "Receptor-mediated antigen delivery into macrophages. Complexing antigen to alpha 2-macroglobulin enhances presentation to T cells." J. Immunol. 150: 48-58.
Chu & Pizzo, 1994, "alpha 2-Macroglobulin, complement, and biologic defense: antigens, growth factors, microbial proteases, and receptor ligation." Lab. Invest. 71:792-812.
Chu et al., 1994, "Adjuvant-free in vivo targeting. Antigen delivery by alpha 2-macroglobulin enhances antibody formation." J. Immunol. 152:1538-1545.
Chu et al., 1994, "Alpha 2-macroglobulin: a sensor for proteolysis." Ann. N.Y. Acad. Sci. 737:291-307.
Craig, 1993, "Chaperones: helpers along the pathways to protein folding." Science 260: 1902-1903.
Ellgaard et al., 1997, "Dissection of the domain architecture of the alpha2macroglobulin-receptor-associated protein." Eur. J. Biochem. 244:544-51.
Fadok et al., 2000, "A receptor for phosphatidylserine-specific clearance of apoptotic cells." Nature 405:85-90.
Gething et al., 1992, "Refolding of yeast enolase in the presence of the chaperonin GroE. The nucleotide specificity of GroE and the role of GroES." Nature 355:33-45.
Greenstone et al., 1996, "Chimeric papillomavirus virus-like particles elicit antitumor immunity against the E7 oncoprotein in an HPV16 tumor model." Proc. Natl. Acad. Sci. USA 95:1800-1805.
Hall et al., 1981, "Proteolytic cleavage sites on alpha 2-macroglobulin resulting in proteinase binding are different for trypsin and *Staphylococcus aureus* V-8 proteinase." Biochem. Biophys. Res. Commun. 100(1):8-16.
Herz et al., 1988, "Surface location and high affinity for calcium of a 500-kd liver membrane protein closely related to the LDL-receptor suggest a physiological role as lipoprotein receptor." EMBO J.: 4119-4127.
Hickey et al., 1989, "Sequence and regulation of a gene encoding a human 89-kilodalton heat shock protein." Mol. Cell. Biol. 9:2615-2626.
Hilliker et al., 1992, "Assignment of the gene coding for the alpha 2-macroglobulin receptor to mouse chromosome 15 and to human chromosome 12q13-q14 by isotopic and nonisotopic in situ hybridization." Genomics 13:472-474.
Holtet et al., 1994, "Receptor-binding domain of human alpha 2-macroglobulin. Expression, folding and biochemical characterization of a high-affinity recombinant derivative." FEBS Lett. 344: 242-246.
Horn et al., 1997, "Molecular analysis of ligand binding to the second cluster of complement-type repeats of the low density lipoprotein receptor-related protein. Evidence for an allosteric component in receptor-associated protein-mediated inhibition of ligand binding." J. Biol. Chem. 272:13608-13613.
Ishii et al., 1999, "Isolation of MHC class I-restricted tumor antigen peptide and its precursors associated with heat shock proteins hsp70, hsp90, and gp96." J. Immunol. 162:1303-1309.
Jindal, 1989, "Primary structure of a human mitochondrial protein homologous to the bacterial and plant chaperonins and to the 65-kilodalton mycobacterial antigen." Mol. Cell. Biol. 9:2279-2283.
Kan et al., 1985, "Nucleotide sequence of cDNA encoding human alpha 2-macroglobulin and assignment of the chromosomal locus." Proc. Natl. Acad. Sci. USA 82: 2282-2286.
Lindquist et al., 1988, "The heat-shock proteins." Annu. Rev. Genetics 22:631-677.
Maki et al., 1993, "Mapping of the genes for human endoplasmic reticular heat shock protein gp96/grp94" Somatic Cell. Mol. Gen. 19:73-81.
Menoret et al., 1999, "Association of peptides with heat shock protein gp96 occurs in vivo and not after cell lysis." Biochem. Biophys. Res. Commun. 262:813-818.

(56) References Cited

OTHER PUBLICATIONS

Mitsuda et al., 1993, "A receptor-mediated antigen delivery and incorporation system. Administration of alpha 2-macroglobulin-cytochrome c conjugate induced high concentrations of antibodies against cytochrome c in mice." Biochem. Biophys. Res. Commun. 101:1326-1331.
Nielsen et al., 1996, "Identification of residues in alpha-macroglobulins important for binding to the alpha2-macroglobulin receptor/Low density lipoprotein receptor-related protein." J. Biol. Chem. 271:12909-12912.
Osada et al., 1987, "Murine T cell proliferation can be specifically augmented by macrophages fed with specific antigen: alpha-2-macroglobulin conjugate." Biochem. Biophys. Res. Commun. 146:26-31.
Osada et al., 1988, "Antibodies against viral proteins can be produced effectively in response to the increased uptake of alpha 2-macroglobulin:viral protein conjugate by macrophages." Biochem. Biophys. Res. Commun. 150: 883.
Otto et al., 1998, "Prostate-specific antigen forms complexes with human alpha 2-macroglobulin and binds to the alpha 2-macroglobulin receptor/LDL receptor-related protein." J. Urol. 159:297-303.
Salvesen et al., "Expression of a functional alpha-macroglobulin receptor binding domain in *Escherichia coli*." 1992, FEBS Lett. 313:198-202.
Savill et al., 1992, "Thrombospondin cooperates with CD36 and the vitronectin receptor in macrophage recognition of neutrophils undergoing apoptosis.." J. Clin. Invest. 90: 1513-1522.
Smordin et al., 1991, "The complex of alpha-2 macroglobulin with CD2 in the plasma of Gastric Carcinoma patients," Scand. J. Immunol. 33(6):699-706.
Srivastava & Old, 1988, "Individually distinct transplantation antigens of chemically induced mouse tumors." Immunol. Today 9:78-83.
Srivastava et al., 1986, "Tumor rejection antigens of chemically induced sarcomas of inbred mice." Proc. Natl. Acad. Sci USA 83:3407-3411.
Srivastava et al., 1988, "Chromosomal assignment of the gene encoding the mouse tumor rejection antigen gp96." Immunogenetics 28: 205-207.
Srivastava et al., 1991, "Stress-induced proteins in immune response to cancer." Curr. Top. Microbiol. Immunol. 167:109-123.
Srivastava et al., 1998, "Heat shock proteins come of age: primitive functions acquire new roles in an adaptive world." Immunity 8:657-665.
Srivastava, 1993, "Peptide-binding heat shock proteins in the endoplasmic reticulum: role in immune response to cancer and in antigen presentation" Adv. Cancer. Res. 62:153-177.
Suto & Srivastava, 1995, "A mechanism for the specific immunogenicity of heat shock protein-chaperoned peptides." Science 269:1585-1588.
Tamura et al., 1997, "Immunotherapy of tumors with autologous tumor-derived heat shock protein preparations." Science 278 (5335):117-120.
Udono & Srivastava, 1993, "Heat shock protein 70-associated peptides elicit specific cancer immunity." J. Exp. Med. 178:1391-1396.
Udono et al., 1994, "Comparison of tumor-specific immunogenicities of stress-induced proteins gp96, hsp90, and hsp70." J. Immunol. 152:5398-5403.

Ullrich et al., 1986, "A mouse tumor-specific transplantation antigen is a heat shock-related protein." Proc. Natl. Acad. Sci. USA 83: 3121-3125.
Welch et al., 1993, "How cells respond to stress." Sci. Amer. 56-64.
Young, 1990, "Stress proteins and immunology." Annu. Rev. Immunol. 8:401-420.
Carswell et al., 1975, "An endotoxin-induced serum factor that causes necrosis of tumors." Proc. Natl. Acad Sci. USA 72(9):3666-3670.
Horssen et al., 2006, "TNF-α in Cancer Treatment: Molecular Insights, Antitumor effects, and Clinical Utility." The Oncol. 11:397-408.
Katsuyuki et al., 1986, "Purification, characterization, and antitumor activity of nonrecombinant mouse tumor necrosis factor." Proc. Natl. Acad. Sci. USA 83:3949-3953.
Kovalchin et al., 2001, "Determinants of efficacy of immunotherapy with tumor-derived heat shock protein gp96." Cancer Immunity 1(7):1-9.
Li et al., 2005, "Combination of Imatinib Mesylate with Autologous Leukocyte-Derived Heat Shock Protein and Chronic Myelogenous leukemia." Clin. Cancer Res 11(12): 4460-4468.
Sato et al., 2001, "Immunotherapy using heat-shock protein preparations of leukemia cells after syngeneic bone marrow transplantation in mice." Blood 98:1852-1857.
Srivastava, 2002, "Interaction of Heat Shock Proteins with Peptides and Antigen Presenting Cells: Chaperoning of the Innate and Adaptive Immune Responses." Annu. Rev. Immunol. 20:395-425.
Testori et al., 2006, "Comparison of Autulogous Tumor-Derived Heat-Shock Protein gp96-Peptide complex vaccine (Vitespen) and Physician's choice in a Randomized Phase 3 Trial in Patients with Stage IV Melanoma." Manuscript submitted, scheduled for publication in the Feb. 20, 2008 issue of Journal of Clinical Oncology.
Wood et al., 2007, "A multicenter, randomized, Phase 3 trial of a Novel autologous therapeutic vaccine (vitespen) vs. observation as adjuvant therapy in patients at high risk or recurrence after nephrectomy for renal cell carcinoma." Amer. Urol. Assoc. Abstract No. 633.
Binder et al., 2004, "Purification of alpha2-macroglobulin and the construction of immunogenic alpha2-macroglobulin-peptide complexes for use as cancer vaccines", Methods; 32(1):29-31.
Hall et al., 1978, "Physical and chemical properties of human plasma $\alpha_2$-Macroglobulin", Biochem. J.; 171:27-38.
Sayegh et al., 1995, "$\alpha_2$-Macroglobulin Production by the Human Endometrium", J. Clin. Endocrinol. Metab.; 80(3):1021-1026.
Srivastava., 1994, "Heat shock proteins in immune response to cancer: The Fourth Paradigm"; Experimentia; 50:1054-1060.
Coombs, 1992, Definition of "purification", Dictionary of Biotechnology, Second Edition; p. 286.
Smith et al., 2000, Definition of "western blotting", Oxford Dictionary of Biochemisty and Molecular Biology Revised Edition; p. 688.
Stenesh, 1989, Definition of "purification", Dictionary of Biochemistry and Molecular Biology Second Edition; p. 393.
Chu et al., 1994, "Alpha 2-macroglobulin: a sensor for proteolysis," Ann N Y Acad Sci. 737:291-307.
Binder et al., 2002, "Naturally formed or artificially reconstituted non-covalent alpha2-macroglobulin-peptide complexes elicit CD91-dependent cellular immunity," Cancer Immun. 2:16.
Laemmli, Cleavage of structural proteins during the assembly of the head of bacteriophage T4. Nature. Aug. 15, 1970;227(5259):680-5.

\* cited by examiner

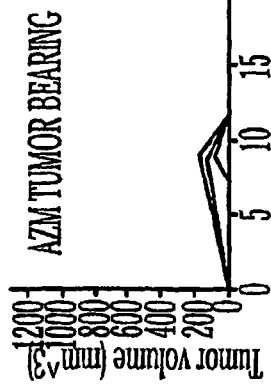
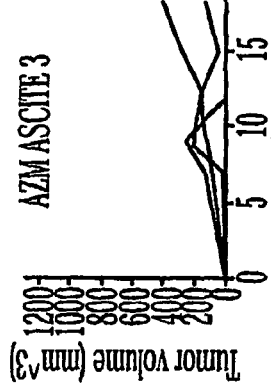
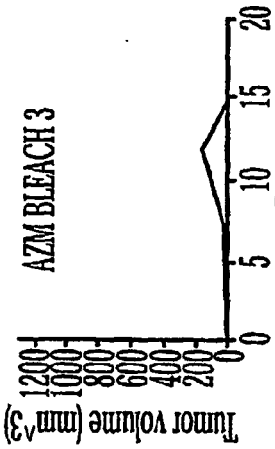
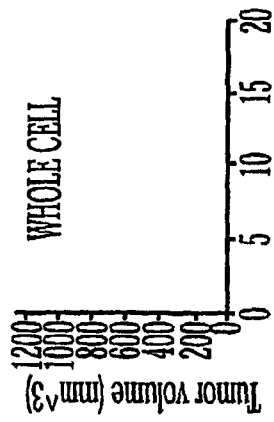
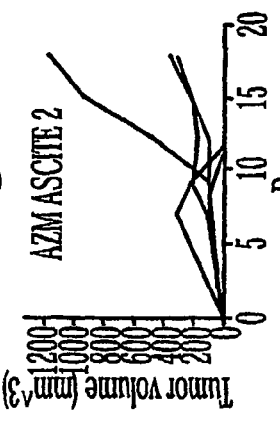
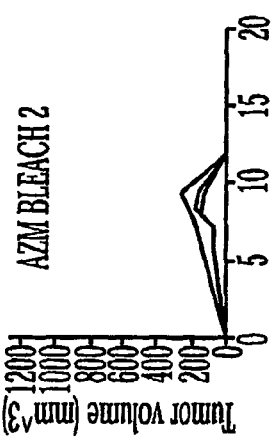
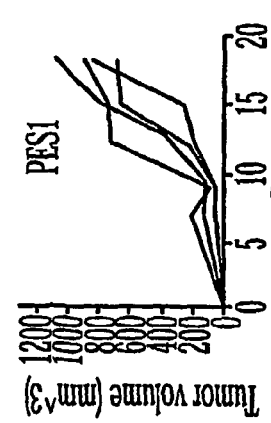
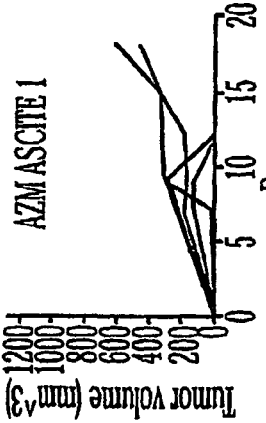
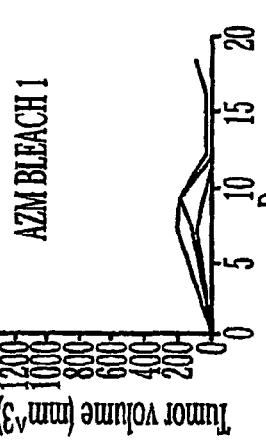

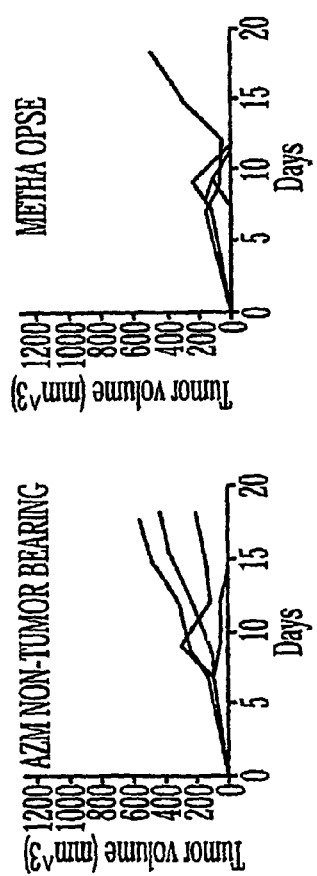
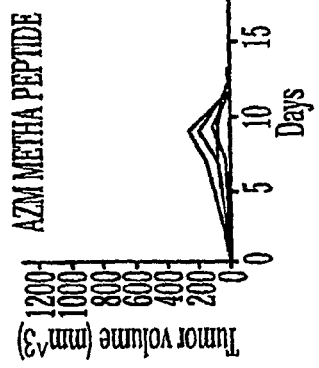
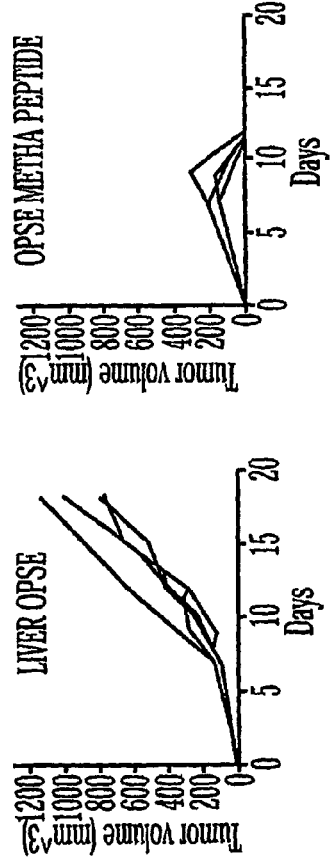
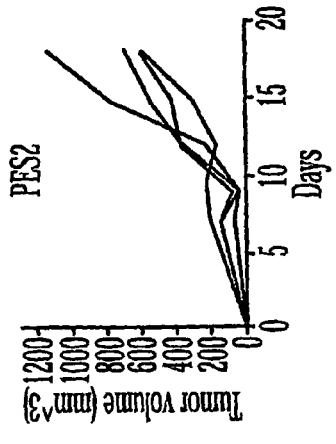
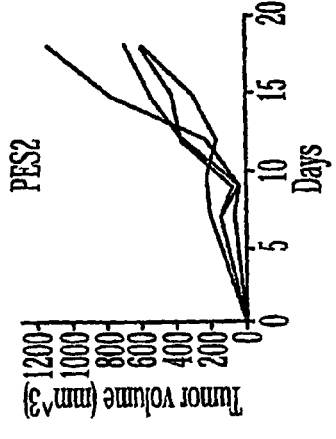

METHODS AND COMPOSITIONS FOR THE TREATMENT OF CANCER AND INFECTIOUS DISEASE USING ALPHA (2) MACROGLOBULIN-ANTIGENIC MOLECULE COMPLEXES

This application claims the benefit of U.S. Provisional Application No. 60/449,022, filed Feb. 20, 2003, and U.S. Provisional Application No. 60/450,751, filed Feb. 27, 2003, each of which is incorporated by reference herein in thier entirety.

The invention was made with government support under grant number CA A184479 awarded by the National Institutes of Health. The government has certain rights in the invention.

1. INTRODUCTION

The present invention relates to the use of alpha (2) macroglobulin complexes isolated from the serum of a mammal in methods for the treatment and prevention of cancer and infectious disease. The invention also encompasses methods for production of alpha (2) macroglobulin complexes. The invention also encompasses compositions and methods for making alpha (2) macroglobulin-antigenic molecule complexes derived from sera.

2. BACKGROUND OF THE INVENTION

2.1. Alpha (2) Macroglobulin

The α-macroglobulins are members of a protein superfamily of structurally related proteins which also comprises complement components C3, C4 and C5. The human plasma protein alpha (2) macroglobulin (α2M) is a 720 kDa homotetrameric protein primarily known as a proteinase inhibitor and plasma and inflammatory fluid proteinase scavenger molecule (for review see Chu and Pizzo, 1994, Lab. Invest. 71:792). α2M is synthesized as a precursor having 1474 amino acid residues. The first 23 amino acids function as a signal sequence that is cleaved to yield a mature protein with 1451 amino acid residues (Kan et al., 1985, Proc. Natl. Acad. Sci. U.S.A. 82:2282-2286).

Alpha (2) macroglobulin promiscuously binds to proteins and peptides with nucleophilic amino acid side chains in a covalent manner (Chu et al., 1994, Ann. N.Y. Acad. Sci. 737:291-307) and targets them to cells which express CD91 (also called the α2M receptor or α2MR; Chu and Pizzo, 1993, J. Immunol. 150:48). Binding of α2M to CD91 is mediated by the carboxy-terminal portion of α2M (Holtet et al., 1994, FEBS Lett. 344:242-246) and key residues have been identified (Nielsen et al., 1996, J. Biol. Chem. 271:12909-12912).

Generally known for inhibiting protease activity, α2M binds to a variety of proteases through multiple binding sites (see, e.g., Hall et al., 1981, Biochem. Biophys. Res. Commun. 100(1):8-16). Protease interaction with α2M results in a complex structural rearrangement called transformation, which is the result of a cleavage within the "bait" region of α2M after the proteinase becomes "trapped" by thioesters. The conformational change exposes residues required for receptor binding, allowing the α2M-proteinase complex to bind to the α2MR. Methylamine can induce similar conformational changes and cleavage as that induced by proteinases. The uncleaved form of α2M, which is not recognized by the receptor, is often referred to as the "slow" form (s-α2M). The cleaved form is referred to as the "fast" form (f-α2M) (reviewed by Chu et al., 1994, Ann. N.Y. Acad. Sci. 737:291-307). Recently, it has also been shown that the α2MR can bind to HSPs, such as gp96, hsp90, hsp70, and calreticulin (Basu et al., 2001, Immunity 14(3):303-13).

Studies have shown that in addition to its proteinase-inhibitory functions, α2M, when complexed to antigens, can enhance the antigens' ability to be taken up by antigen presenting cells such as macrophages and presented to T cell hybridomas in vitro by up to two orders of magnitude (Chu and Pizzo, 1994, Lab. Invest. 71:792), and to induce T cell proliferation (Osada et al., 1987, Biochem. Biophys. Res. Commun. 146:26-31). Further evidence suggests that complexing antigen with α2M enhances antibody production by crude spleen cells in vitro (Osada et al., 1988, Biochem. Biophys. Res. Commun. 150:883), elicits an in vivo antibody responses in experimental rabbits (Chu et al., 1994, J. Immunol. 152:1538-1545) and mice (Mitsuda et al., 1993, Biochem. Biophys. Res. Commun. 101:1326-1331). α2M-antigenic peptide complexes have also been shown to induce a cytotoxic T cell response in vivo (Binder et al., 2001, J. Immunol. 166:4698-49720).

2.2. Heat Shock Proteins

Heat shock proteins (HSPs), also referred to as stress proteins, were first identified as proteins synthesized by cells in response to heat shock. Hsps have been classified into five families, based on molecular weight, Hsp100, Hsp90, Hsp70, Hsp60, and smHsp. Many members of these families were found subsequently to be induced in response to other stressful stimuli including nutrient deprivation, metabolic disruption, oxygen radicals, and infection with intracellular or extracellular pathogens (see Welch, 1993, Scientific American 56-64; Young, 1990, Annu. Rev. Immunol. 8:401-420; Craig, 1993, Science 260:1902-1903; Gething et al., 1992, Nature 355:33-45; and Lindquist et al., 1988, Annu. Rev. Genetics 22:631-677).

Heat shock proteins are among the most highly conserved proteins in existence. For example, DnaK, the Hsp70 from *E. coli* has about 50% amino acid sequence identity with Hsp70 proteins from excoriates (Bardwell et al., 1984, Proc. Natl. Acad. Sci. 81:848-852). The Hsp60 and Hsp90 families also show similarly high levels of intra-family conservation (Hickey et al., 1989, Mol. Cell. Biol. 9:2615-2626; Jindal, 1989, Mol. Cell. Biol. 9:2279-2283). In addition, it has been discovered that the Hsp60, Hsp70 and Hsp90 families are composed of proteins that are related to the stress proteins in sequence, for example, having greater than 35% amino acid identity, but whose expression levels are not altered by stress.

Studies on the cellular response to heat shock and other physiological stresses revealed that the HSPs are involved not only in cellular protection against these adverse conditions, but also in essential biochemical and immunological processes in unstressed cells. HSPs accomplish different kinds of chaperoning functions. For example, members of the Hsp70 family, located in the cell cytoplasm, nucleus, mitochondria, or endoplasmic reticulum (Lindquist et al, 1988, Ann. Rev. Genetics 22:631-677), are involved in the presentation of antigens to the cells of the immune system, and are also involved in the transfer, folding and assembly of proteins in normal cells. HSPs are capable of binding proteins or peptides, and releasing the bound proteins or peptides in the presence of adenosine triphosphate (ATP) or low pH.

2.3. Immunogenicity of HSP-Peptide Complexes

Srivastava et al demonstrated immune response to methylcholanthrene-induced sarcomas of inbred mice (1988, Immunol. Today 9:78-83). In these studies, it was found that the molecules responsible for the individually distinct immunogenicity of these tumors were glycoproteins of 96 kDa (gp96) and intracellular proteins of 84 to 86 kDa (Srivastava et al., 1986, Proc. Natl. Acad. Sci. USA 83:3407-3411; Ullrich et al., 1986, Proc. Natl. Acad. Sci. USA 83:3121-3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava et al., 1988, Immunogenetics 28:205-207; Srivastava et al., 1991, Curr. Top. Microbiol. Imunol. 167:109-123). Further, Hsp70 was shown to elicit immunity to the tumor from which it was isolated but not to antigenically distinct tumors. However, Hsp70 depleted of peptides was found to lose its immunogenic activity (Udono and Srivastava, 1993, J. Exp. Med. 178:1391-1396). These observations suggested that the heat shock proteins are not immunogenic per se, but form noncovalent complexes with antigenic peptides, and the complexes can elicit specific immunity to the antigenic peptides (Srivastava, 1993, Adv. Cancer Res. 62:153-177; Udono et al., 1994, J. Immunol., 152:5398-5403; Suto et al., 1995, Science, 269:1585-1588).

Noncovalent complexes of HSPs and peptide, purified from cancer cells, can be used for the treatment and prevention of cancer and have been described in PCT publications WO 96/10411, dated Apr. 11, 1996, and WO 97/10001, dated Mar. 20, 1997 (U.S. Pat. No. 5,750,119 issued Apr. 12, 1998, and U.S. Pat. No. 5,837,251 issued Nov. 17, 1998, respectively, each of which is incorporated by reference herein in its entirety). The isolation and purification of stress protein-peptide complexes has been described, for example, from pathogen-infected cells, and can be used for the treatment and prevention of infection caused by the pathogen, such as viruses, and other intracellular or extracellular pathogens, including bacteria, protozoa, fungi and parasites (see, for example, PCT Publication WO 95/24923, dated Sep. 21, 1995). Immunogenic stress protein-peptide complexes can also be prepared by in vitro complexing of stress protein and antigenic peptides, and the uses of such complexes for the treatment and prevention of cancer and infectious diseases has been described in PCT publication WO 97/10000, dated Mar. 20, 1997 (U.S. Pat. No. 6,030,618 issued Feb. 29, 2000. The use of stress protein-peptide complexes for sensitizing antigen presenting cells in vitro for use in adoptive immunotherapy is described in PCT publication WO 97/10002, dated Mar. 20, 1997 (see also U.S. Pat. No. 5,985,270 issued Nov. 16, 1999).

2.4. The Alpha (2) Macroglobulin Receptor, or "CD91"

The alpha (2) macroglobulin receptor herein referred to interchangeably as either "α2MR" or "the α2M receptor"), also known as LDL (low-density lipoprotein) receptor-Related Protein ("LRP") or CD91, is primarily expressed in liver, brain and placenta. The α2M receptor is a member of the low density lipoprotein receptor family. The extracellular domain of the human receptor comprises six 50-amino acid EGF repeats and 31 complement repeats of approximately 40-42 amino acids. The complement repeats are organized, from the amino to the carboxy-terminus, into clusters of 2, 8, 10 and 11 repeats, called Cluster I, II, III and IV (Herz et al., 1988, EMBO J. 7:4119-4127). One study points to Cluster II (Cl-III), which contains complement repeats 3-10 (CR3-10), as the major ligand binding portion of the receptor (Horn et al., 1997, J. Biol. Chem. 272:13608-13613). The α2M receptor plays a role in endocytosis of a diversity of ligands. In addition to α2M, other ligands of α2MR include lipoprotein complexes, lactoferrin, tissue-type plasminogen activator (tPA), urokinase-type plasminogen activator (uPA), and exotoxins. Additional examples of ligands of α2MR can be found in PCT publication WO 97/04794 and U.S. Pat. No. 6,156, 311. Thus, the α2M receptor plays roles in a variety of cellular processes, including endocytosis, antigen presentation, cholesterol regulation, ApoE-containing lipoprotein clearance, and chylomicron remnant removal.

Human α2M is synthesized as a 1474 amino acid precursor, the first 23 of which function as a signal sequence that is cleaved to yield a 1451 amino acid mature protein (Kan et al., 1985, Proc. Natl. Acad. Sci. U.S.A. 82:2282-2286). In experiments with recombinant protein, the carboxy-terminal 138 amino acids of α2M (representing amino acids 1314-1451 of the mature protein) was found to bind the receptor. This domain has been called the RBD (receptor-binding domain; Salvesent et al., 1992, FEBS Lett. 313:198-202; Holtet et al., 1994, FEBS Lett. 344:242-246). An RBD variant (RBDv), a proteolytic fragment of α2M comprising an additional 15 amino terminal residues (representing amino acids 1314-1451 of the mature protein) binds to the receptor with almost the same affinity as α2M-proteinase (Holtet et al., 1994, FEBS Lett. 344:242-246).

Alignment of α2MR ligands identifies a conserved domain present in the RBDs of α macroglobulins. The conserved sequence spans amino acids 1366-1392 of human α2M. Conserved residues within this domain are $Phe_{1366}$, $Leu_{1369}$, $Lys_{1370}$, $Val_{1373}$, $Lys_{1374}$, $Glu_{1377}$, $Val_{1382}$, $Arg_{1384}$ (Nielsen et al., 1996, J. Biol. Chem. 271:12909-12912). Of these, $Lys_{1370}$ and $Lys_{1374}$ were shown to be critical for receptor binding (Nielsen et al., 1996, J. Biol. Chem. 271:12909-12912).

Binding of ligands, including the binding to α2M, to α2MR is inhibited by α2MR-associated protein (RAP). RAP is a 39 kDa folding chaperone that resides in the endoplasmic reticulum and is required for the normal processing of α2MR. RAP has the ability to competitively inhibit the binding of all α2MR to all α2MR ligands tested. One study shows RAP to bind to complement repeats C5-C7 in cluster II (Cl-II) of α2MR (Horn et al., 1997, J. Biol. Chem. 272:13608-13613); another shows RAP to bind to all two complement repeat-modules in Cl-II except the C9-C10 module (Andersen et al., J. Biol. Chem., Mar. 24, 2000, PMID: 10747921; published electronically ahead of print). Three structural domains, 1, 2 and 3, have been identified in RAP, consisting of amino acid residues 18-112, 113-218 and 219-323, respectively. Ligand competition titration of recombinant RAP domains indicates that determinants for the inhibition of test ligands reside in the C-terminal regions of domains 1 and 3 (Ellgaard et al., 1997, Eur. J. Biochem. 244:544-51).

The use of CD91 as a heat shock protein receptor, cells that express CD91 bound to an HSP, antibodies and other molecules that bind a CD91-HSP complex, screening assays to identify compounds that modulate the interaction of an HSP with CD91, methods for using compositions comprising CD91, and CD91 sequences for the diagnosis and treatment of immune disorders, proliferative disorders, and infectious diseases have also been described in PCT publication WO 01/92474, dated Dec. 6, 2001. Complexes of alpha (2) macroglobulin associated with antigenic molecules for use in immunotherapy and methods for using such compositions in the diagnosis and treatment of proliferative disorders, and infectious diseases have also been described in PCT publication WO 01/91787 dated Dec. 6, 2001. Binder et al. showed that in vitro reconstituted complexes of alpha (2) macroglobulin and antigenic peptides elicit specific CTL response (Binder et al, 2001, J. Immunol. 166:4968-4972).

2.5. Antigen Presentation

Major histocompatibility complex (MHC) molecules present antigens on the cell surface of antigen-presenting cells. Antigens are processed by two distinct antigen processing routes depending upon whether their origin is intracellular or extracellular. Intracellular or endogenous protein antigens, i.e., antigens synthesized within the antigen-presenting cell, are presented by MHC class I (MHC I) molecules to CD8+ cytotoxic T lymphocytes. On the other hand, extracellular or exogenously synthesized antigenic determinants are presented on the cell surface of "specialized" or "professional" APCs (macrophages, for example) by MHC class II molecules to CD4+ T cells (see, generally, Fundamental Immunology, W. E. Paul (ed.), New York: Raven Press, 1984). This compartmental segregation of antigen processing routes is important to prevent tissue destruction that could otherwise occur during an immune response as a result of shedding of neighboring cell MHC I antigens.

The heat shock proteins chaperone a wide array of peptides, depending upon the source from which the HSP is isolated (for review, see Srivastava et al., 1998, Immunity 8: 657-665). Tumor-derived HSP carries tumor-antigenic peptides (Ishii et al., 1999, J. Immunology 162:1303-1309); gp96 preparations from virus-infected cells carry viral epitopes (Suto and Srivastava, 1995, Science 269:1585-1588; Nieland et al., 1996, Proc. Natl. Acad. Sci. USA 95:1800-1805), and gp96 preparations from cells transfected with model antigens such as ovalbumin or β-galactosidase are associated with the corresponding epitopes (Arnold et al., 1995, J. Exp. Med. 182:885-889; Breloer et al., 1998, Eur. J. Immunol. 28:1016-1021). The association of gp96 with peptides occurs in vivo (Menoret and Srivastava, 1999, Biochem. Biophys. Research Commun. 262:813-818). HSP-peptide complexes, whether isolated from cells (Tamura et al., 1997, Science 278:117-120), or reconstituted in vitro (Blachere et al., 1997, J. Exp. Med. 186:1183-1406) are excellent immunogens and have been used extensively to elicit CD8+ T cell responses specific for the HSP-chaperoned antigenic peptides.

The capacity of HSP-peptide complexes to elicit an immune response is dependent upon the transfer of the peptide to MHC class I molecules of antigen-presenting cells (see for example: Suto and Srivastava, 1995, supra). Endogenously synthesized antigens chaperoned by gp96 in the endoplasmic reticulum [ER] can prime antigen-specific CD8+ T cells (or MHC I-restricted CTLs) in vivo; this priming of CD8+ T cells requires macrophages. However, the process whereby exogenously introduced gp96-peptide complexes elicit the antigen-specific CD8+ T cell response is not completely understood since there is no established pathway for the translocation of extracellular antigens into the class I presentation machinery. Yet antigenic peptides of extracellular origin associated with HSPs are somehow salvaged by macrophages, channeled into the endogenous pathway, and presented by MHC I molecules to be recognized by CD8+ lymphocytes (Suto and Srivastava, 1995, supra; Blachere et al., 1997, J. Exp. Med. 186:1315-22).

2.6. HSP-CD91 Interactions

The studies reported by Basu et al. indicate that the heat shock proteins gp96, hsp90, hsp70, and calreticulin are additional ligands for the CD91 (Basu et al., 2001, supra). Gp96 engages a region of CD91, located in an amino terminal fragment termed the p80 fragment (Binder et al, 2000, Nature immunology, 1:151-155; WO 01/92474). The human gp96-coding gene has been mapped previously by us at chromosome 12 (q24.2 q24.3) (Maki et al., 1993, Somatic Cell Mol. Gen. 19:73-81). It is of interest in this regard that the CD91 gene has been mapped to the same chromosome and at a not too distant location (q13 q14) (Hilliker et al. Genomics 13:472-474). Gp96 binds CD91 directly and not through other ligands such as α2M. Homogenous preparations of gp96, in solution, or cross-linked to a solid matrix, bind to the CD91. Indeed, the major ligand for the CD91, α2M, actually inhibits interaction of gp96 with CD91, instead of promoting it, providing evidence that gp96 is a direct ligand for the CD91. The 80 kDa protein, p80, shown to bind gp96 is clearly an amino terminal degradation product of the α subunit of the CD91 (Binder et al, 2000, Nature immunology, 1: 151-155). Degradation products of the CD91 in this size range have also been observed in previous studies (Jensen et al., 1989, Biochem. Arch. 5:171-176), and may indicate the existence of a discrete ectodomain in the CD91 which may be particularly sensitive to proteolytic cleavage.

The observations of Basu et al. that α2 macroglobulin and anti-CD91 antibodies inhibit re-presentation by each of the four HSPs completely, indicate that CD91 is the only receptor for the 4 HSPs (Basu et al., 2001, supra). Considering the increasingly obvious role which the HSPs play in innate (Basu et al., 2000, Int. Immunol. 12(11):1539-1546) and adaptive immune response, this observation is somewhat counter-intuitive. However, the data on complete inhibition by two independent means are quite compelling (PCT publication WO 01/92474, dated Dec. 6, 2001). Binder reported significant differences between hsp70 and hsp90/gp96 in their ability to compete for binding to gp96 receptors (Binder et al., 2000, J. Imunol. 165:2582-2587). Another group has also observed similar differences between gp96 and hsp70 (Arnold-Schild et al., 1999, 162:3757-3760). These differences are not inconsistent with Basu's report pointing to a single receptor for the 4 HSPs. They simply suggest that the various HSPs interact with a single receptor with widely differing affinities As shown in Binder et al., the heat shock protein-CD91 interaction provides a new type of function for CD91, or a fragment thereof, a function of a sensor, not only of the extracellular environment with its previously known plasma-based ligands, but also a sensor of the intracellular milieu as well. HSPs such as gp96 are obligate intracellular molecules and are released into the extracellular milieu only under conditions of necrotic (but not apoptotic) cell death (PCT publication WO 01/92474, dated Dec. 6, 2001). Thus, the CD91 may act as a sensor for necrotic cell death, just as the scavenger receptor CD36 and the recently identified phosphatidyl serine-binding protein act as sensors of apoptotic cell death and receptors for apoptotic cells (Savill et al., 1992, J. Clin. Invest. 90:1513-1522; Fadok et al., 2000, Nature 405:85-90). Interaction of the macrophages with the apoptotic cells leads to a down-regulation of the inflammatory cytokines such as TNF (Fadok et al., 2000, supra), while gp96-APC interaction leads to re-presentation of gp96-chaperoned peptides by MHC I molecules of the APC, followed by stimulation of antigen-specific T cells (Suto and Srivastava, 1995, supra) and, in addition, secretion of pro-inflammatory cytokines such as TNF, GM-CSF and IL-12. Interestingly, α2M, an independent ligand for the CD91, inhibits representation of gp96-chaperoned peptides by macrophages. This observation of Binder suggests that re-presentation of gp96-chaperoned peptides can not occur physiologically in blood, but only within tissues as a result of localized necrotic cell death. This is consistent with the complete absence of gp96 or other HSPs in blood under all conditions tested. Together, Binder's observations point towards a possible mechanism whereby the release of HSPs in the blood as a result of severe tissue injury and lysis will not lead to a systemic and lethal pro-inflammatory cytokine cascade.

It is possible, therefore, that CD91 renders it possible for the APCs to sample (i) the extracellular milieu of the blood through α2M and other plasma ligands and (ii) the intracellular milieu of the tissues through HSPs, particularly of the gp96 family. The former permits APCs to implement their primordial phagocytic function, while the latter allows them to execute its innate and adaptive immunological functions. Viewed in another perspective, recognition of apoptotic cells by APCs through CD36 or phophatidyl serine, leads to anti-inflammatory signals, while interaction of the APC with necrotic cells through CD91 leads to pro-inflammatory innate and adaptive immune responses (see Srivastava et al., 1998, Immunity 8: 657-665).

Citation or discussion of a reference herein shall not be construed as an admission that such is prior art to the present invention.

3. SUMMARY OF THE INVENTION

The present invention relates to methods and compositions for treating and preventing cancer and infectious disease using complexes of alpha (2) macroglobulin and antigenic molecules, which complexes are derived from the bodily fluid of a patient having cancer or an infectious disease. In a preferred embodiment of the invention, the alpha (2) macroglobulin-antigenic molecule complexes are autologous to the patient being treated. The invention is based, in part, on the Applicants' discovery that alpha (2) macroglobulin antigenic molecule complexes specific to tumor or a pathogen can be found in, and isolated from, the blood stream of subjects having cancer or an infectious disease. Furthermore, Applicants discovered that such alpha (2) macroglobulin-antigenic molecule complexes can be isolated in sufficient amounts from the bloodstream of patients for use in autologous immunotherapy. In the field of cancer therapy, this discovery enables the preparation of highly specific, individualized immunotherapeutics which target specific antigens expressed on each individual patient's tumor, without having to first characterize or identify such antigens. Such autologous immunotherapy using alpha (2) macroglobulin complexes is shown herein to be highly efficacious in both the treatment and prevention of cancer. Moreover, such results can be extended to applications for treating and preventing infectious disease.

The Applicants discovered that female C57BL/6 mice immunized with alpha (2) macroglobulin complexes purified from male mice mount anti-male responses (Binder et al., 2002, Cancer Immunity, Vol. 2:16). Alpha (2) macroglobulin-male antigen complexes were obtained and used for priming immune responses. Binder et al. demonstrated that the Y antigen which is expressed in male mice, can be isolated in a form complexed to alpha (2) macroglobulin from the sera of normal male mice. Binder et al. then applied this basic concept to cancer immunity and demonstrated that the immunity evoked by alpha (2) macroglobulin-peptide complexes reconstituted in vitro was effective in prophylaxis against tumors (Binder et al., 2002, supra).

Most tumors do not produce alpha (2) macroglobulin, and even those that do produce alpha (2) macroglobulin, such as tumors of hepatocyte origin, produce alpha (2) macroglobulin intracellularly. The present invention, based in part on the Applicants' discovery that tumors or pathogen-bearing cells shed antigens into bodily fluids, e.g. blood, where they can form complexes with alpha (2) macroglobulin.

The present invention provides a method for treating or preventing cancer or infectious disease in a patient, said method comprising administering to a patient in need of said treatment or prevention an amount of a complex of alpha (2) macroglobulin and an antigenic molecule effective to treat or prevent cancer or infectious disease in a patient, wherein said complex was isolated from a bodily fluid of a mammal having cancer or an infectious disease.

The invention further provides a method for treating or preventing cancer or infectious disease in a patient comprising the steps of: a) isolating a complex of alpha (2) macroglobulin and an antigenic molecule from a bodily fluid of a mammal having said cancer or infectious disease; and b) administering an amount of said isolated complex effective to treat or prevent said cancer or infectious disease in said patient. In a specific embodiment, the complex is a population of complexes of alpha (2) macroglobulin bound to different antigenic molecules in which the different antigenic molecules comprise one which has the antigenicity of an antigen specific to said cancer or infectious disease. In another specific embodiment, the method is for treating cancer and patient has cancer, and the antigenic molecule is derived from a tumor. In another specific embodiment of the invention, the method is for treating cancer and the patient has cancer, and the efficacy of said cancer treatment is assessed by a decrease in tumor size or a decrease in the number of tumors in the patient. In another specific embodiment, the method is for preventing cancer and the patient is in need of such prevention, and said antigenic molecule displays an antigen having the antigenicity of an antigen specific to said cancer. In yet another specific embodiment, the method is for preventing an infectious disease and the patient is in need of such prevention, and said antigenic molecule displays an antigen having the antigenicity of an antigen specific to a pathogen associated with said infectious disease. In yet another embodiment, the method is for treating cancer and the patient has cancer and the method further comprises, prior to or at the same time as step (b), the step of administering a chemotherapeutic agent to said patient. In another specific embodiment, the method is for treating cancer and the patient has cancer, and the method further comprises, prior to or at the same time as step (a), the step of inducing tumor necrosis in said mammal. In another specific embodiment, the step of inducing tumor necrosis comprises administering to said mammal a tumor-necrosis agent.

In another embodiment, the invention provides a method for stimulating an immune response against cancer or an infectious disease in a in a patient comprising: a) isolating alpha (2) macroglobulin complexes from a bodily fluid of a mammal, and b) administering the isolated alpha (2) macroglobulin complexes to the patient such that an immune response is stimulated. In a specific embodiment, the patient is a human patient. In another specific embodiment, the alpha (2) macroglobulin complexes are a population of complexes of alpha (2) macroglobulin bound to different antigenic molecules in which the different antigenic molecules comprise one which has the antigenicity of an antigen specific to said cancer or infectious disease. In another specific embodiment, the method is for stimulating an immune response against cancer in a patient which has cancer, and the method further comprising, prior to or at the same time as step (a), the step of inducing tumor necrosis in said mammal. In another specific embodiment, the step of inducing tumor necrosis comprises administering to said mammal a tumor-necrosis agent.

The invention further provides a method for preventing cancer in a mammal, said method comprising administering an effective amount of a complex of alpha (2) macroglobulin and an antigenic molecule, said complex isolated from a bodily fluid of said mammal, said mammal having a precancerous lesion or polyp. In a specific embodiment of the method, the mammal is a human.

The invention further provides a method for preventing cancer in a first mammal, said method comprising administering an effective amount of a complex of alpha (2) macroglobulin and an antigenic molecule, said complex isolated from a bodily fluid of a second mammal, said second mammal having a precancerous lesion or polyp. In a specific embodiment, the complex comprises a plurality of complexes comprising alpha (2) macroglobulin bound to one or more different antigenic molecules in which the different antigenic molecules comprise at least one which has the antigenicity of an antigen specific to said cancer or infectious disease. In another specific embodiment, the complex is autologous to said patient. In another specific embodiment, said complex is purified prior to administration. In another specific embodiment, said bodily fluid is vascular fluid. In another specific embodiment, the vascular fluid is serum derived from blood. In yet another specific embodiment, the bodily fluid is extravascular ascites or cerebral spinal fluid.

In another embodiment of the invention, a pharmaceutical composition is provided comprising (a) a plurality of alpha (2) macroglobulin-antigenic molecule complexes isolated from a bodily fluid of a mammal having cancer or an infectious disease, said plurality comprising at least one complex comprising an alpha (2) macroglobulin and an antigenic molecule which displays an antigen having the antigenicity of an antigen specific to a tumor or an infectious agent; and (b) an effective amount of a pharmaceutical carrier. In a specific embodiment, the bodily fluid is vascular fluid serum. In another specific embodiment, the vascular fluid is serum derived from blood. In yet another specific embodiment, bodily fluid is extravascular ascites or cerebral spinal fluid.

The invention further provides a vaccine comprising: (a) a plurality of alpha (2) macroglobulin-antigenic molecule complexes isolated from a bodily fluid of a mammal having a precancerous lesion or a polyp, said plurality comprising at least one complex comprising an alpha (2) macroglobulin and an antigenic molecule which displays an antigen having the antigenicity of an antigen specific to a tumor; and (b) an effective amount of a pharmaceutical carrier. In a specific embodiment, the plurality of alpha (2) macroglobulin-antigenic molecule complexes is purified.

In another embodiment of the invention, a pharmaceutical composition is provided comprising: (a) a complex comprising an alpha (2) macroglobulin and an antigenic molecule having the antigenicity of a tumor or infectious disease; (b) an agent selected from the group consisting of: an HSP-peptide complex, an anti-neoplastic agent, an antibody, a cytokine, an antiviral, an anti-fungal, an antibiotic, and a chemotherapeutic agent; and (c) an effective amount of a pharmaceutical carrier. In a specific embodiment, the agent is a chemotherapeutic agent. In another specific embodiment, the alpha (2) macroglobulin-antigenic molecule complex is purified.

The invention further provides a method for increasing the presence of a complex comprising alpha (2) macroglobulin and an antigenic molecule in a bodily fluid of a mammal, said method comprising inducing tumor necrosis in said mammal. In a specific embodiment, the step of inducing tumor necrosis comprises administering to said mammal a tumor-necrosis agent.

In another embodiment, the invention provides a kit comprising in one or more containers therapeutically or prophylactically effective amounts of covalent or non-covalent alpha (2) macroglobulin-antigenic molecule complexes in pharmaceutically acceptable form.

The invention further provides a method for increasing the presence of a complex comprising alpha (2) macroglobulin and an antigenic molecule in a bodily fluid of a mammal, said method comprising inducing tumor necrosis in said mammal.

In another embodiment, the invention provides a method for preparing a complex comprising an alpha (2) macroglobulin and an antigenic molecule having the antigenicity of a precancerous lesion, a tumor or an infectious disease comprising: a) withdrawing serum from a patient having a precancerous lesion, tumor or infectious disease; and b) recovering an alpha (2) macroglobulin-antigenic molecule complex from said serum. In a specific embodiment, the method is for treating or preventing cancer and said method further comprising the step of administering to said patient an amount of the recovered complexes effective to treat or prevent cancer. In a specific embodiment of the method, the step of recovering an alpha (2) macroglobulin-antigenic molecule complex from said serum comprises: a) contacting a solid phase containing an alpha (2) macroglobulin-binding molecule with the serum for a time period sufficient to allow binding of the alpha (2) macroglobulin-antigenic molecule complex with the solid phase; b) removing material not bound to the solid phase; and c)eluting the bound alpha (2) macroglobulin-antigenic molecule complex from the solid phase. In a specific embodiment, the alpha (2) macroglobulin-binding molecule is an antibody specific to alpha (2) macroglobulin. In another specific embodiment, the alpha (2) macroglobulin-binding molecule is a ligand-binding fragment of CD91.

The invention further provides a method for preparing a complex comprising an alpha (2) macroglobulin and an antigenic molecule having the antigenicity of a precancerous lesion, a tumor or an infectious disease comprising: a) withdrawing serum from a patient having a precancerous lesion, tumor or infectious disease; and b) fractionating the serum to enrich for an alpha (2) macroglobulin-antigenic molecule complex. In a specific embodiment, the step of contacting the serum with an agent which stimulates covalent bond formation between the alpha (2) macroglobulin and the antigenic molecule. In another specific embodiment, the agent is a protease, ammonia, methyamine or ethylamine.

In various embodiments, the bodily fluid of the methods of the invention is a vascular fluid. In other embodiments, the vascular fluid is serum derived from blood. In yet other embodiments, the bodily fluid is extravascular ascites or cerebral spinal fluid.

As referred to herein, "alpha (2) macroglobulin" refers to an alpha (2) macroglobulin polypeptide, as well as peptide-binding fragments, derivatives, mimetics and analogues thereof.

The terms "complex comprising alpha (2) macroglobulin and an antigenic molecule" or "an alpha (2) macroglobulin-antigenic molecule complex", used interchangeably herein, refer to an alpha (2) macroglobulin protein or polypeptide, or peptide-binding fragment thereof, associated with an antigenic molecule. The association can be a covalent or non-covalent bond between the alpha (2) macroglobulin protein or polypeptide and the antigenic molecule.

As used herein, the term "bodily fluid" means any fluid of the body which can be used for preparation of alpha (2) macroglobulin-antigenic molecule complexes. Bodily fluids include vascular and extravascular fluid. Extravascular fluids include, but are not limited to, ascites fluid, cerebral fluid, tissue lymph fluid, colostrum, and semen. In a preferred embodiment, the bodily fluid is blood. In a specific preferred embodiment, the body fluid is serum isolated from blood.

4. BRIEF DESCRIPTION OF THE FIGURE

FIG. 1 The figure shows graphs representing the size growth of tumors (mm3) over an 18 day period in groups of mice immunized with alpha (2) macroglobulin complexes.

Naive mice were immunized to determine if the complexes would provide a prophylactic effect. A, mice immunized with PBS as negative control, called PBS1; B, mice immunized with irradiated Meth A tumor cells; C-F, 3 groups of mice (labeled "ASCITES 1-3") (5 mice per group) immunized with alpha (2) macroglobulin-antigenic molecule complexes from serum of mice bearing intradermal Meth A tumors; G-I, 3 groups of mice (labeled "BLEACH 1-3") (5 mice per group) immunized with alpha (2) macroglobulin-antigenic molecule complexes from serum of tumor-bearing mice where the tumors were treated with bleach; J, mice immunized with alpha (2) macroglobulin-antigenic molecule complexes from serum of non-tumor bearing mice; K, mice immunized with MethA derived gp96; L, mice immunized with α2M complexed to MethA10 (peptides<10 kDa derived from MethA tumor lysate); M, mice immunized with liver derived gp96; N, mice immunized with gp96 complexed to MethA10, called gp 96-MethA10; and O, mice immunized with PBS, called PBS2.

5. DETAILED DESCRIPTION OF THE INVENTION

The present invention relates to compositions and methods for the use of alpha (2) macroglobulin-antigenic molecule complex isolated from sera of a mammal in treating and preventing cancer or infectious disease. The invention encompasses methods for use of alpha (2) macroglobulin-antigenic molecule complex derived from the bodily fluid of a patient having cancer or infectious disease to treat or prevent said cancer or infectious disease. Such methods include autologous treatment methods for cancer and infectious disease and vaccines for prevention of cancers and infectious diseases. The invention also encompasses pharmaceutical compositions comprising a plurality of alpha (2) macroglobulin-antigenic molecule complex, and pharmaceutical compositions comprising alpha (2) macroglobulin-antigenic molecule complex together with a therapeutic agent for treatment of a cancer or infectious disease. A method of increasing the presence of alpha (2) macroglobulin-antigenic molecule complex in the serum of a mammal is also encompassed by the invention.

5.1. Pharmaceutical Compositions of the Invention

The present invention provides pharmaceutical compositions comprising alpha (2) macroglobulin complexes isolated from serum of a mammal, that can be used to treat and/or prevent a cancer or infectious disease. Such compositions may, optionally, also comprise agents commonly used for therapeutic treatment of cancer and infectious diseases such as, but not limited to, an HSP-peptide complex, an antineoplastic agent, an antibody, a cytokine, an antiviral, an anti-fugal, an antibiotic, or a chemotherapeutic agent. The pharmaceutical compositions of the invention can also include the agents described in Section 5.4 for targeting cancer, Section 5.5 for targeting infectious diseases and Section 5.3.3 for targeting cancer and infectious disease with combination therapies. The pharmaceutical compositions of the invention also include pharmaceutical carriers such as those described in Section 5.9. The pharmaceutical compositions of the invention are particularly effective in autologous therapies. Such pharmaceutical compositions can also include adjuvants, and/or agents that induce or increase production of antigenic molecules. In certain embodiments, the agent causes tumor necrosis. Methods for the production of such pharmaceutical compositions are described herein. Methods for increasing the presence of antigenic molecules and/or alpha (2) macroglobulin-antigenic molecule complexes in the serum prior to or in conjunction with isolation of such complexes are also described herein.

The pharmaceutical compositions and methods of the invention comprise complexes of alpha (2) macroglobulin with a population of antigenic peptides. The pharmaceutical compositions appear to induce an inflammatory reaction at the tumor site and can ultimately cause a regression of the tumor burden in the cancer patients treated. The compositions prepared by the methods of the invention can enhance the immunocompetence of the subject and elicit specific immunity against infectious agents or specific immunity against preneoplastic and neoplastic cells. These compositions have the capacity to prevent the onset and progression of infectious diseases, and to inhibit the growth and progression of tumor cells.

In specific embodiments, an α2M complex is administered to a subject receiving another treatment modality for the treatment of cancer or infectious disease wherein the subject may be non-responsive or refractory to treatment with the treatment modality alone, i.e., at least some significant portion of cancer cells or pathogens are not killed or their cell division is not arrested. The determination of the effectiveness of a treatment modality can be assayed in vivo or in vitro using methods known in the art. Art-accepted meanings of refractory are well known in the context of cancer. In one embodiment, a cancer or infectious disease is refractory or non-responsive where respectively, the number of cancer cells or pathogens has not been significantly reduced, or has increased. Among these subjects being treated are those receiving chemotherapy or radiation therapy.

In certain embodiments the compositions of the invention comprise alpha (2) macroglobulin-antigenic molecule complexes that are purified. In such embodiments, the alpha (2) macroglobulin-antigenic molecule complexes are at least 30%, 40%, 50%, 60%, 70%, 80%, 90% or 100% purified.

5.2. Preparation of Alpha (2) Macroglobulin Complexes

Generally, the alpha (2) macroglobulin-antigenic molecule complexes of the invention can be recovered and purified from sera of mammals by known methods, including ammonium sulfate precipitation, acid extraction, anion or cation exchange chromatography, phosphocellulose chromatography, immunoaffinity chromatography, hydroxyapatite chromatography, and lectin chromatography.

In one embodiment, alpha (2) macroglobulin-antigenic molecule complexes are purified from serum using affinity purification techniques. Methods for chromatography fractionation of proteins, such as affinity chromatography, are well known in the art. Briefly, affinity chromatography utilizes an immobilized binding partner to specifically capture the protein in the binding reaction. The binding partner molecule of the affinity capture assay can comprise, for example, an antibody to alpha (2) macroglobulin, or other ligand, such as a CD91 binding domain which specifically binds alpha (2) macroglobulin. Alternatively, a filter binding assay utilizes a device, such as a solid phase surface such as a filter or a column, to non-specifically retain proteins or protein complexes based on some physical or chemical difference between the complexes and the unbound reactants. Affinity chromatography and/or filter binding separation techniques may be used to isolate alpha (2) macroglobulin-antigenic molecule complexes from serum or other bodily fluid as described herein.

In a specific embodiment of the invention, alpha (2) macroglobulin-antigenic molecule complexes are isolated from serum as follows: serum is contacted to a solid phase, such as an agarose column, which contains a binding partner of alpha (2) macroglobulin, i.e., an alpha (2) macroglobulin-binding molecule. The serum is allowed to incubate on the solid phase for a period of time sufficient to allow binding of the alpha (2) macroglobulin-antigenic molecule complex with the solid phase. The material which does not bind is then removed from the solid phase; and the bound alpha (2) macroglobulin-antigenic molecule complex is eluted from the solid phase.

The binding partner of alpha (2) macroglobulin may be any molecule which specifically binds to alpha (2) macroglobulin. In a preferred embodiment, the alpha (2) macroglobulin-binding molecule is an antibody specific to alpha (2) macroglobulin. The alpha (2) macroglobulin-specific antibody is preferably a monoclonal antibody. In another preferred embodiment, the alpha (2) macroglobulin-binding molecule is a ligand-binding fragment of CD91.

The solid phase may be any surface or matrix, such as, but not limited to, polycarbonate, polystyrene, polypropylene, polyethylene, glass, nitrocellulose, dextran, nylon, polyacrylamide and agarose. The support configuration can include beads, membranes, microparticles, the interior surface of a reaction vessel such as a microtiter plate, test tube or other reaction vessel.

In a preferred embodiment, the alpha (2) macroglobulin-antigenic molecule complexes are isolated from serum from mice by diluting serum 1:1 with 0.04 M Tris pH 7.6, 0.15 M NaCl. The mixture is then applied to a Sephacryl S 300R (Sigma) column equilibrated and eluted with the same buffer. A 65 ml column is used for about 10 ml of serum. Alpha (2) macroglobulin-positive fractions are determined by dot blot and the buffer changed to a 0.01 M sodium phosphate buffer at pH 7.5 by use of a PD-10 column. In an alternative method, the 0.01 M sodium phosphate buffer at pH 7.5 can be used as buffer in the 65 ml column to eliminate the step of exchanging the buffer. The complex-containing fractions are applied to a Concanavalin A sepharose column. Bound complexes are eluted with 0.2 M methylmannose pyranoside, or 5% methylmannose pyranoside, and applied to a PD-10 column to change the buffer to 0.05 M sodium acetate buffer pH 6.0, and applied to a DEAE column equilibrated with 0.01 M sodium acetate buffer pH 6.0. Alpha (2) macroglobulin are eluted in a pure form with 0.13 M sodium acetate buffer, and analyzed by SDS-PAGE and immunoblotting.

The embodiments described above may be used to recover and purify alpha (2) macroglobulin-antigenic molecule complexes from the serum of mammalian cells, such as blood containing an alpha (2) macroglobulin-antigenic molecule complex of the invention. The methods can be adapted to perform medium and large scale purification of an alpha (2) macroglobulin-antigenic molecule complex. Methods that do not require lowering pH or denaturing conditions are most preferred for purification of alpha (2) macroglobulin-antigenic molecule complexes. The methods may be used to isolate alpha (2) macroglobulin-antigenic molecule complexes from eukaryotic cells, for example, cancer cells, tissues, isolated cells, or immortalized eukaryote cell lines infected with an intracellular or extracellular pathogen, or cells obtained from a subject infected with a pathogen.

In applying the methods for isolation and purification described above, one of skill in the art will be aware that use of agents and conditions that are too stringent, might disassociate the complexes.

In another embodiment, complexes of α2M polypeptides and antigenic molecules isolated from serum are treated to covalently complex α2M polypeptides with an antigenic peptides prior to their administration to patients. Procedures for forming such covalent α2M-antigenic molecule complexes are described in detail herein.

In general, when an α2M is mixed with protease, cleavage of the "bait" region of α2M takes place, the proteinase becomes "trapped" by thioesters, and a conformational change takes place that allows binding of the α2M complex to the CD91. During proteolytic activation of α2M, non-proteolytic ligands can become covalently bound to the activated thioesters. Non-proteolytic ligands can also be incorporated into the activated α2M molecule by ammonia or methylamine during reversal of the nucleophilic activation, employing heat (Grøn and Pizzo, 1998, Biochemistry, 37: 6009-6014). Such conditions that allow fortuitous trapping of peptides by α2M are employed to prepare the α2M-antigenic complexes of the invention. Methods for such covalent coupling have been described previously (Osada et al., 1987, supra; Osada et al., 1988, supra; Chu and Pizzo, 1993, supra; Chu et al., 1994, supra; Mitsuda et al., 1993, supra).

For example, in a specific embodiment, fractionated serum enriched for α2M polypeptides and antigenic molecules (which may or may not be covalently bound) are mixed in the presence of a protease, ammonia or other small amine nucleophiles such as methylamine and ethylamine. Non-limiting examples of proteases which may be used include trypsin, porcine pancreatic elastase (EP), human neutrophil elastase, cathepsin G, S. aureus V-8 proteinase trypsin, a-chymotrypsin, V8 protease, papain, and proteinase K (see Ausubel et al., (eds.), in "Current Protocols in Molecular Biology," Greene Publishing Associates and Wiley Interscience, New York, 17.4.6-17.4.8). A preferred, exemplary protocol for covalently complexing α2M polypeptides and an antigenic molecules present in sera is provided herein. In a specific embodiment, the following protocol may be used to increase the quantity of α2M-antigenic molecule covalent complexes. The fractionated sera (100µ-5 ml) comprising α2M antigenic molecule complexes (1 µg-20 mg) is treated with methylamine, or a protease such as trypsin (0.92 mg trypsin in approximately 500 ml PBS (phosphate-buffered saline). The mixture is then incubated for 5-15 minutes to 37° C. If trypsin is used, 500 ml 4 mg/ml p-Aphenyl methyl sulfonyl fluoride (p-APMSF) is then added to the solution to inhibit trypsin activity, and incubated for 2 hrs at 25° C. Optionally, free antigenic molecules may be removed by passage over a gel permeation column.

Following complexing, the immunogenic α2M-antigenic molecule complexes can optionally be assayed in vitro using, for example, the mixed lymphocyte target cell assay (MLTC) described below. Once immunogenic complexes have been isolated they can be optionally characterized further in animal models using the preferred administration protocols and excipients discussed below prior to their administration.

In a preferred embodiment, the alpha (2) macroglobulin-antigenic molecule complexes are isolated from serum from mice by diluting serum 1:1 with 0.04 M Tris pH 7.6, 0.15 M NaCl. The mixture is then applied to a Sephacryl S 300R (Sigma) column equilibrated and eluted with the same buffer. A 65 ml column is used for about 10 ml of serum. Alpha (2) macroglobulin-positive fractions are determined by dot blot and the buffer changed to a 0.01 M sodium phosphate buffer at pH 7.5 by use of a PD-10 column. In an alternative method, the 0.01 M sodium phosphate buffer at pH 7.5 can be used as buffer in the 65 ml column to eliminate the step of exchanging the buffer. The complex-containing fractions are applied to a Concanavalin A sepharose column. Bound complexes are eluted with 0.2 M methylmannose pyranoside, or 5% methylmannose pyranoside, and applied to a PD-10 column to change the buffer to 0.05 M sodium acetate buffer pH 6.0, and applied to a DEAE column equilibrated with 0.01 M sodium acetate buffer pH 6.0. Alpha (2) macroglobulin are eluted in a pure form with 0.13 M sodium acetate buffer, and analyzed by SDS-PAGE and immunoblotting. Other methods for isolation of complexes known in the art can also be used (Dubin et al, 1984, Biochem. International 8(4):589-596; Okubo et al., 1981, Biochem. et Biophys. Acta 688:257-267; Nieuwenhuizen et al. 1979, Biochem. et Biophysica. Acta 580:129-139).

5.3. Therapeutic Uses 5.3.1. Methods for Treatment and Prevention of Cancer

According to the invention, preferred methods of treatment or prevention of cancer comprise isolating α2M complexes from the individual in need of treatment, and administering such complexes to the patient as a form of autologous therapy. Depending on the route of administration, the α2M complexes are isolated and purified and administered to the individual autologously (e.g., to treat the primary cancer or metastases thereof), or to other individuals who are in need of treatment for cancer of a similar tissue type, or to individuals at enhanced risk of cancer due to familial history or environmental risk factors. Cancers described in Section 5.4 can be treated or prevented by using the pharmaceutical compositions and methods of the invention.

For example, treatment with compositions of the invention comprising α2M complexes isolated from the serum of a patient and prepared as described above may be started any time after surgery. In other embodiments, the treatment can begin before surgery, or during. However, if the patient has received chemotherapy, α2M complexes are usually administered after an interval of four weeks or more so as to allow the immune system to recover. The therapeutic regimen may include weekly injections of the compositions of the invention comprising α2M complex, dissolved in saline or other physiologically compatible solution. The route and site of injection is varied each time, for example, the first injection is given subcutaneously on the left arm, the second injection on the right arm, the third injection on the left abdominal region, the fourth injection on the right abdominal region, the fifth injection on the left thigh, the sixth injection on the right thigh, etc. The same site is repeated after a gap of one or more injections. In addition, injections are split and each half of the dose is administered at a different site on the same day. Overall, the first four to six injections are given at weekly intervals. Subsequently, two to fifty injections are given at two-week intervals, followed by a regimen of injections at monthly intervals.

Alternatively, α2M complexes isolated from the serum of the patient can be used as a vaccine for prevention of cancer. Such vaccines can be used by injection into a patient to stimulate an immune response against the tumor cells, cells bearing tumor antigens. Autologous α2M polypeptide-antigenic molecule complexes are preferred. Vaccines of the invention can be administered prior to, during or after chemotherapy.

In a specific embodiment, the cancer is metastatic. In another specific embodiment, the cancer is a tumor.

The effect of immunotherapy with α2M polypeptide-antigenic molecule complexes on progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology and density of tumors using techniques such as a computed tomographic (CT) scan; e) measuring the change in diameter of tumors using CT scan; f) measuring the changes in levels of putative biomarkers of risk for a particular cancer in individuals at high risk, g) measuring the percentage of necrotic tissue in a tumor before and after treatment, h) measuring the changes in the morphology of tumors using a sonogram, i) measuring the changes in the morphology of tumors using magnetic resonance imaging (MRI), j) measuring the changes in the morphology of tumors using positron emission tomography (PET), and k) measuring the changes in the morphology of tumors using ultrasound. Other techniques that can also be used include scintigraphy and endoscopy.

The preventive effect of immunotherapy using α2M polypeptide-antigenic molecule complexes may also be estimated by determining levels of a putative biomarker for risk of a specific cancer. For example, in individuals at enhanced risk for prostate cancer, serum prostate-specific antigen (PSA) is measured by the procedure described by Brawer et al., 1992, J. Urol. 147:841-845, and Catalona et al., 1993, JAMA 270:948-958; or in individuals at risk for colorectal cancer, CEA is measured by methods known in the art; and in individuals at enhanced risk for breast cancer, 16-hydroxylation of estradiol is measured by the procedure described by Schneider et al., 1982, Proc. Natl. Acad. Sci. USA 79:3047-3051. The references cited above are incorporated by reference herein in their entirety.

In a specific embodiment, the preventive and therapeutic utility of the invention is directed at enhancing the immunocompetence of the cancer patient either before surgery, at or after surgery, and at inducing tumor-specific immunity to cancer cells, with the objective being inhibition of cancer, and with the ultimate clinical objective being total cancer regression and eradication.

In accordance with the invention, a composition of the invention, which comprises complexes of antigenic peptides derived from digested cytosolic and/or membrane-derived proteins of antigenic cells. Alpha (2) macroglobulin, is administered to a subject with cancer In one embodiment, "treatment" or "treating" refers to an amelioration of cancer, or at least one discernible symptom thereof. In another embodiment, "treatment" or "treating" refers to an amelioration of at least one measurable physical parameter associated with cancer, not necessarily discernible by the subject. In yet another embodiment, "treatment" or "treating" refers to inhibiting the progression of a cancer, either physically, e.g., stabilization of a discernible symptom, physiologically, e.g., stabilization of a physical parameter, or both.

In certain embodiments, the compositions of the present invention are administered to a subject as a preventative measure against such cancer. As used herein, "prevention" or "preventing" refers to a reduction of the risk of acquiring a given cancer. In one mode of the embodiment, the compositions of the present invention are administered as a preventative measure to a subject having a genetic predisposition to a cancer. In another mode of the embodiment, the compositions of the present invention are administered as a preventive measure to a subject facing exposure to carcinogens including but not limited to chemicals and/or radiation.

For example, in certain embodiments, administration of the compositions of the invention lead to an inhibition or reduction of the growth of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth in absence of said composition.

The compositions prepared by methods of the invention comprise complexes of complexes of alpha-2-macroglobulin with a population of antigenic peptides. The compositions appear to induce reduction in tumor size and can ultimately cause a regression of the tumor burden in the cancer patients treated. The compositions prepared by the methods of the invention can enhance the immunocompetence of the subject and elicit specific immunity against preneoplastic and neoplastic cells. These compositions have the capacity to prevent the growth and progression of tumor cells.

In certain embodiments of the methods of the invention, alpha (2) macroglobulin-antigenic molecule complexes are administered to patients with a familial history of cancer, or to individuals at risk for development of cancer due to environmental factors. In other embodiments, patients with precancerous lesions or polyps are treated using the methods of the invention as a prophylactic, based on the discovery by Applicants that complexes can be isolated from serum which are effective against cancers that could potentially develop. In other embodiments, patients are treated using the methods of the invention, based on the discovery that undetectable early cancers leads to the presence of alpha (2) macroglobulin-antigenic molecule complexes that would be useful in preventing cancer development. In other embodiments, patients, in which cancer is not yet detectable are treated using the methods of the invention, as a prophylactic measure.

5.3.2. Methods for Treatment and Prevention of Infectious Diseases

For treatment and prevention of infectious disease, α2M-antigenic molecule complexes are isolated from the bodily fluid of a mammal having an infectious disease, and used as vaccines against the infectious disease. As will be appreciated by those skilled in the art, the protocols described herein may be used to isolate α2M polypeptide-antigenic molecule complexes from any bodily fluid where alpha (2) macroglobulin-anitgenic molecule complexes are present. For example, cells may be infected by the infectious agent itself. In one embodiment, α2M-antigenic molecule complexes can be isolated from serum that comprises antigens from agents infecting cells. In another embodiment, the α2M-antigenic molecule complexes of the invention can be isolated from serum that comprises antigens derived from an intracellular or extracellular pathogen. The invention is not limited to treating or preventing infectious diseases caused by intracellular or extracellular pathogens. Many medically relevant microorganisms have been described extensively in the literature, e.g., see G. L. Mandell, J. E. Bennet, and R. Dolin, Mandell, Douglas, and Bennett's Principles and Practice of Infectious Diseases, Churchill Livingstone, Phillidelphia, Pa. 2000, the entire contents of which is hereby incorporated by reference.

A preferred method for treatment or prevention of an infectious disease comprises isolating alpha (2) macroglobulin complex from the serum of a patient and administering the isolated complex to the patient at a time when the patient is in need of treatment. Complexes of α2M polypeptides covalently or noncovalently associated with antigenic molecules of the infectious agent are purified from the serum.

In a preferred aspect of the invention, the purified α2M-antigenic molecule complex vaccines may have particular utility in the treatment of human diseases caused by intracellular or extracellar pathogens. It is appreciated, however, that the vaccines developed using the principles described herein will be useful in treating diseases of other mammals, for example, farm animals including: cattle; horses; sheep; goats; and pigs, and household pets including: cats; and dogs, that similarly are caused by intracellular or extracellular pathogens.

Vaccines may be prepared that stimulate immune responses to any of the infectious disease pathogens described in Section 5.5. The effect of immunotherapy with modified α2M polypeptide-antigenic molecule complexes on progression of infectious diseases can be monitored by any methods known to one skilled in the art.

The compositions prepared by methods of the invention comprise complexes of alpha (2) macroglobulin with a population of antigenic peptides. The compositions prepared by the methods of the invention can enhance the immunocompetence of the subject and elicit specific immunity against infectious agents. These compositions have the capacity to prevent the onset and progression of infectious diseases.

In one embodiment, "treatment" or "treating" refers to an amelioration of an infectious disease, or at least one discernible symptom thereof. In another embodiment, "treatment" or "treating" refers to an amelioration of at least one measurable physical parameter associated with an infectious disease, not necessarily discernible by the subject. In yet another embodiment, "treatment" or "treating" refers to inhibiting the progression of a an infectious disease, either physically, e.g., stabilization of a discernible symptom, physiologically, e.g., stabilization of a physical parameter, or both.

The compositions prepared by methods of the invention comprise complexes of alpha-2-macroglobulin with a population of antigenic peptides. The compositions prepared by the methods of the invention can enhance the immunocompetence of the subject and elicit specific immunity against infectious agents. These compositions have the capacity to prevent the onset and progression of infectious diseases.

In certain embodiments, the compositions of the present invention are administered to a subject as a preventative measure against such an infectious disease. As used herein, "prevention" or "preventing" refers to a reduction of the risk of acquiring a given infectious disease. In another mode of the embodiment, the compositions of the present invention are administered as a preventive measure to a subject facing exposure to an agent of an infectious disease.

For example, in certain embodiments, administration of the compositions of the invention lead to an inhibition or reduction of the growth of infectious agents by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth in absence of said composition.

5.3.3. Combination Therapy for Treatment and Prevention of Cancer and Infectious Diseases The compositions and methods of the invention using alpha (2) macroglobulin complexes can be administered in conjunction with other therapeutic agents as a combination therapeutic regime. Other therapeutic agents include, but are not limited to heat shock protein-peptide complexes, anti-neoplastic agents, antibodies, cytokines, anti-virals/fungals/biotics and adjuvants.

Combination therapy refers to the use of α2M complexes of the invention with another modality to prevent or treat cancer and/or infectious diseases. In the context of treating and preventing cancer, combination therapy refers to the use of α2M complexes of the invention with another modality to prevent or treat cancer. The administration of the complexes of the invention can augment the effect of anti-cancer agents, and vice versa. In the context of treating and preventing infectious disease, the administration of the complexes of the invention can augment the effect of anti-infectives, and vice versa. Preferably, this additional form of modality is a non-α2M based modality, i.e., this modality does not comprise α2M as a component. This approach is commonly termed combination therapy, adjunctive therapy or conjunctive therapy (the terms are used interchangeably herein). With combination therapy, additive potency or additive therapeutic effect can be observed. Synergistic outcomes where the therapeutic efficacy is greater than additive can also be expected. The use of combination therapy can also provide better therapeutic profiles than the administration of the treatment modality, or the α2M complexes alone. The additive or synergistic effect may allow the dosage and/or dosing frequency of either or both modalities be adjusted to reduce or avoid unwanted or adverse effects.

In various specific embodiments, the combination therapy comprises the administration of α2M-antigenic molecule complexes to a subject treated with a treatment modality wherein the treatment modality administered alone is not clinically adequate to treat the subject such that the subject needs additional effective therapy, e.g., a subject is unresponsive to a treatment modality without administering α2M complexes. Included in such embodiments are methods comprising administering α2M complexes to a subject receiving a treatment modality wherein said subject has responded to therapy yet suffers from side effects, relapse, develops resistance, etc. Such a subject might be non-responsive or refractory to treatment with the treatment modality alone, i.e., at least some significant portion of cancer cells are not killed or their cell division is not arrested or at least some significant portion of pathogens or infectious agents are not killed. The methods of the invention comprising administration of an α2M complexes to a subject refractory to a treatment modality alone can also improve the therapeutic effectiveness of the treatment modality when administered as contemplated by the methods of the invention. The determination of the effectiveness of a treatment modality can be assayed in vivo or in vitro using methods known in the art.

Art-accepted meanings of refractory are well known in the context of cancer and infectious disease. In one embodiment, a cancer is refractory or non-responsive where respectively, the number of cancer cells has not been significantly reduced, or has increased. In another embodiment, an infectious disease is refractory or non-responsive where respectively, the number of pathogens has not been significantly reduced, or has increased.

According to the invention, complexes of the invention can be used in combination with many different types of treatment modalities. Some of such modalities are particularly useful for a specific type of cancer or infectious disease and are discussed in Section 5.4 and 5.5, respectively. Many other modalities have an effect on the functioning of the immune system and are applicable generally to both neoplastic and infectious diseases.

In one embodiment, complexes of the invention are used in combination with one or more biological response modifiers to treat cancer or infectious disease. One group of biological response modifiers is the cytokines. In one such embodiment, a cytokine is administered to a subject receiving α2M complexes. In various embodiments, one or more cytokine(s) can be used and are selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, TGF-β, IL-15, IL-18, GM-CSF, INF-γ, INF-α, SLC, endothelial monocyte activating protein-2 (EMAP2), MIP-3α, MIP-3β, or an MHC gene, such as HLA-B7. Additionally, other exemplary cytokines include other members of the TNF family, including but not limited to TNF-α-related apoptosis-inducing ligand (TRAIL), TNF-α-related activation-induced cytokine (TRANCE), TNF-α-related weak inducer of apoptosis (TWEAK), CD40 ligand (CD40L), lymphotoxin alpha (LT-α), lymphotoxin beta (LT-β), OX40 ligand (OX40L), Fas ligand (FasL), CD27 ligand (CD27L), CD30 ligand (CD30L), 41BB ligand (41BBL), APRIL, LIGHT, TL1, TNFSF16, TNFSF17, and AITR-L, or a functional portion thereof. See, e.g., Kwon et al., 1999, Curr. Opin. Immunol. 11:340-345 for a general review of the TNF family. Preferably, the α2M complexes are administered prior to the treatment modalities. In a specific embodiment, complexes of the invention are administered to a subject receiving cyclophosphamide in combination with IL-12 for treatment of cancer.

In another embodiment, complexes of the invention are used in combination with one or more biological response modifiers which are agonists or antagonists of various ligands, receptors and signal transduction molecules. For example, the biological response modifiers include, but are not limited to, agonists of Toll-like receptors (TLR-2, TLR-7, TLR-8 and TLR-9; LPS; agonists of 41BB, OX40, ICOS, and CD40; and antagonists of Fas ligand, PD1, and CTLA-4. These agonists and antagonists can be antibodies, antibody fragments, peptides, peptidomimetic compounds, and polysaccharides.

In yet another embodiment, complexes of the invention are used in combination with one or more biological response modifiers which are immunostimulatory nucleic acids. Such nucleic acids, many of which are oligonucleotides comprising an unmethylated CpG motif, are mitogenic to vertebrate lymphocytes, and are known to enhance the immune response. See Woolridge, et al., 1997, *Blood* 89:2994-2998. Such oligonucleotides are described in International Patent Publication Nos. WO 01/22972, WO 01/51083, WO 98/40100 and WO 99/61056, each of which is incorporated herein in its entirety, as well as U.S. Pat. Nos. 6,207,646, 6,194,388, 6,218,371, 6,239,116, 6,429,199, and 6,406,705, each of which is incorporated herein in its entirety. Other kinds of immunostimulatory oligonucleotides such as phosphorothioate oligodeoxynucleotides containing YpG- and CpR-motifs have been described by Kandimalla et al. in "Effect of Chemical Modifications of Cytosine and Guanine in a CpG-Motif of Oligonucleotides: Structure-Immunostimulatory Activity Relationships." Bioorganic & Medicinal Chemistry 9:807-813 (2001), incorporated herein by reference in its entirety. Also encompassed are immunostimulatory oligonucleotides that lack CpG dinucleotides which when administered by mucosal routes (including low dose administration) or at high doses through parenteral routes, augment antibody responses, often as much as did the CpG nucleic acids, however the response was Th2-biased (IgG1>>IgG2a). See United States Patent Publication No. 20010044416 A1, which is incorporated herein by reference in its entirety. Methods of determining the activity of immunostimulatory oligonucleotides can be performed as described in the aforementioned patents and publications. Moreover, immunostimulatory oligonucleotides can be modified within the phosphate backbone, sugar, nucleobase and internucleotide linkages in order to modulate the activity. Such modifications are known to those of skill in the art.

In yet another embodiment, complexes of the invention are used in combination with one or more adjuvants. The adjuvant(s) can be administered separately or present in a composition in admixture with complexes of the invention. A systemic adjuvant is an adjuvant that can be delivered parenterally. Systemic adjuvants include adjuvants that creates a depot effect, adjuvants that stimulate the immune system and adjuvants that do both. An adjuvant that creates a depot effect as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

Other adjuvants stimulate the immune system, for instance, cause an immune cell to produce and secrete cytokines or IgG. This class of adjuvants includes but is not limited to immunostimulatory nucleic acids, such as CpG oligonucleotides; saponins purified from the bark of the *Q. saponaria* tree, such as QS21; poly[di(carboxylatophen-oxy) phosphazene (PCPP polymer; Virus Research Institute, USA); derivatives of lipopolysaccharides (LPS) such as monophosphoryl lipid A (MPL; Ribi ImmunoChem Research, Inc., Hamilton, Mont.), muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). In a preferred embodiment, complexes of the invention are used in combination with QS21 and another immunostimulatory nucleic acid such as, but not limited to a CG oligonucleotide.

Other systemic adjuvants are adjuvants that create a depot effect and stimulate the immune system. These compounds are those compounds which have both of the above-identified functions of systemic adjuvants. This class of adjuvants includes but is not limited to ISCOMs (Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

The mucosal adjuvants useful according to the invention are adjuvants that are capable of inducing a mucosal immune response in a subject when administered to a mucosal surface in conjunction with complexes of the invention. Mucosal adjuvants include but are not limited to CpG nucleic acids (e.g. PCT published patent application WO 99/61056), Bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), *Pertussis* toxin, PT. (Lycke et al., 1992, Spangler B D, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); bacterial outer membrane proteins (e.g., outer surface protein A (OspA) lipoprotein of *Borrelia burgdorferi*, outer membrane protine of *Neisseria meningitidis*)(Marinaro et al., 1999, Van de Verg et al., 1996); oil-in-water emulsions (e.g., MF59) (Barchfield et al., 1999, Verschoor et al., 1999, O'Hagan, 1998); aluminum salts (Isaka et al., 1998, 1999); and Saponins (e.g., QS21) Aquila Biopharmaceuticals, Inc., Worster, Me.) (Sasaki et al., 1998, MacNeal et al., 1998), ISCOMs, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micell-forming agent; IDEC Pharmaceuticals Corporation, San Diego, Calif); Syntext Adjuvant Formulation (SAF; Syntex Chemicals, Inc., Boulder, Colo.); poly[di(carboxylatophenoxy)phosphazene (PCPP polymer; Virus Research Institute, USA) and *Leishmania* elongation factor (Corixa Corporation, Seattle, Wash.).

In another embodiment, complexes of the invention are administered in combination with one or more immunotherapeutic agents, such as antibodies and vaccines. In a preferred embodiment, the antibodies have in vivo therapeutic and/or prophylactic uses against cancer and/or infectious disease. Examples of therapeutic and prophylactic antibodies include, but are not limited to, MDX-010 (Medarex, NJ) which is a humanized anti-CTLA-4 antibody currently in clinic for the treatment of prostate cancer; SYNAGIS® (MedImmune, MD) which is a humanized anti-respiratory syncytial virus (RSV) monoclonal antibody for the treatment of patients with RSV infection; HERCEPTIN® (Trastuzumab) (Genentech, CA) which is a humanized anti-HER2 monoclonal antibody for the treatment of patients with metastatic breast cancer. Other examples are a humanized anti-CD 18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti Hepatitis B virus antibody (Protein Design Lab/Novartis); PROTOVIR™ which is a humanized anti-CMV IgG1 antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (InClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genentech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); DEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-αFab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/Tanox Biosystems); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); and Corsevin M is a chimeric anti-Factor VII antibody (Centocor). In a preferred embodiment, complexes of the invention are administered in combination with anti-CTLA4 antibodies. In another preferred embodiment, complexes of the invention are administered in combination with anti-41BB antibodies. The above-listed immunoreactive reagents, as well as any other immunoreactive reagents, may be administered according to any regimen known to those of skill in the art, including the regimens recommended by the suppliers of the immunoreactive reagents.

In the context of treatment or prevention of infectious disease, alpha (2) macroglobulin-antigenic molecule complexes are administered to patients at risk for development of infectious disease due to environmental or familial factors. In other embodiments, patients with early symptoms of infectious disease are treated using the methods of the invention as a prophylactic, based on the concept that complexes can be isolated from serum which are effective against infectious disease that could potentially develop. In other embodiments, patients without infectious disease symptoms are treated using the methods of the invention, based on the belief that undetectable early infections of pathogens might lead to the presence of alpha (2) macroglobulin-antigenic molecule complexes that would be useful in preventing development of the infectious disease. In other embodiments, healthy patients, are treated using the methods of the invention, as a prophylactic measure based on the concept that a patient might have infectious disease forms that are not yet detectable.

To determine the effectiveness of the compositions and methods of the invention one skilled in the art can use standard assays for detection of infection, including but not limited to, antibody titer assays, measurement of viral load using PCR technology, for example, to detect viral specific nucleic acids, blood cell analysis, plaque assays, phage assays, or culturing of bacterial samples. Such methods for detecting and measuring levels of infection are well know to those of skill in the art.

In another embodiment, in the context of treatments and prophylactic methods for cancer, each of the above methods comprise the administration of an α2M complex, preferably a purified α2M complex, to a subject receiving a combination of treatment modalities for the treatment of cancer. Preferably, the α2M complex is associated with an antigenic molecule which displays the antigenicity of the type of cancer being treated.

5.4. Target Cancers

In one embodiment, the methods of the invention and combination therapies thereof encompass, administration of the compositions of the invention comprising one or more modalities for adjuvant use that aid in the prevention or treatment of cancer, which modalities include, but are not limited to, chemotherapeutic agents, immunotherapeutics, anti-angiogenic agents, cytokines, hormones, antibodies, polynucleotides, radiation and photodynamic therapeutic agents. In specific embodiments, combination therapy involving administration of pharmaceutical compositions of the invention can be used to prevent the recurrence of cancer, inhibit metastasis, or inhibit the growth and/or spread of cancer or metastasis.

Types of cancers that can be treated or prevented by the methods and pharmaceutical compositions of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

There are many reasons why immunotherapy as provided by the present invention is desired for use in cancer patients. First, if cancer patients are immunosuppressed, surgery with anesthesia and subsequent chemotherapy may worsen the immunosuppression. With appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

The preventive and therapeutic methods of the invention are directed at enhancing the immunocompetence of the cancer patient either before surgery, at or after surgery, and to induce tumor-specific immunity to cancer cells, with the objective being inhibition of cancer, and with the ultimate clinical objective being total cancer regression and eradication. The methods and pharmaceutical compositions of the invention can also be used in individuals at enhanced risk of a particular type of cancer, e.g., due to familial history or environmental risk factors.

In various embodiments, one or more anti-cancer agent, in addition to the complexes of the invention, is administered to treat a cancer patient. An anti-cancer agent refers to any molecule or compound that assists in the treatment of tumors or cancer. Examples of anti-cancer agents that may be used in the methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs that can be used include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides;

insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

An anti-cancer agent can be a chemotherapeutic agents which include but are not limited to, the following groups of compounds:cytotoxic antibiotics, antimetabolities, anti-mitotic agents, alkylating agents, platinum compounds, arsenic compounds, DNA topoisomerase inhibitors, taxanes, nucleoside analogues, plant alkaloids, and toxins; and synthetic derivatives thereof. Table 1 lists exemplary compounds of the groups:

TABLE 1

| Alkylating agents | |
|---|---|
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| Platinum containing compounds: | Cisplatin |
| | Carboplatin |
| | Aroplatin |
| | Oxaliplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxol |
| DNA Topoisomerase Inhibitors | |
| Epipodophyllins: | Etoposide |
| | Teniposide |
| | Topotecan |
| | 9-aminocamptothecin |
| | Camptothecin |
| | Crisnatol |
| mitomycins: | Mitomycin C |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonucleotide reductase Inhibitors: | Hydroxyurea |
| | Deferoxamine |
| Pyrimidine analogs: | |
| Uracil analogs: | 5-Fluorouracil |
| | Floxuridine |
| | Doxifluridine |
| | Ratitrexed |
| Cytosine analogs: | Cytarabine (ara C) |
| | Cytosine arabinoside |
| | Fludarabine |

TABLE 1-continued

| | |
|---|---|
| Purine analogs: | Mercaptopurine |
| | Thioguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |
| | beta-TGDR |
| | cyclocytidine |
| | guanazole |
| | inosine glycodialdehyde |
| | macebecin II |
| | pyrazoloimidazole |
| Antimitotic agents: | allocolchicine |
| | Halichondrin B |
| | colchicine |
| | colchicine derivative |
| | dolstatin 10 |
| | maytansine |
| | rhizoxin |
| | thiocolchicine |
| | trityl cysteine |
| Others: | |
| Isoprenylation inhibitors: | |
| Dopaminergic neurotoxins: | 1-methyl-4-phenylpyridinium ion |
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | Verapamil |
| $Ca^{2+}$ ATPase inhibitors: | Thapsigargin |

Compositions comprising one or more chemotherapeutic agents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone. Each of the foregoing lists is illustrative, and is not intended to be limiting.

In one embodiment, breast cancer can be treated with a pharmaceutical composition comprising complexes of the invention in combination with 5-fluorouracil, cisplatin, docetaxel, doxorubicin, Herceptin®, gemcitabine, IL-2, paclitaxel, and/or VP-16 (etoposide).

In another embodiment, prostate cancer can be treated with a pharmaceutical composition comprising complexes of the invention in combination with paclitaxel, docetaxel, mitoxantrone, and/or an androgen receptor antagonist (e.g., flutamide).

In another embodiment, leukemia can be treated with a pharmaceutical composition comprising complexes of the invention in combination with fludarabine, cytosine arabinoside, gemtuzumab (MYLOTARG), daunorubicin, methotrexate, vincristine, 6-mercaptopurine, idarubicin, mitoxantrone, etoposide, asparaginase, prednisone and/or cyclophosphamide. As another example, myeloma can be treated with a pharmaceutical composition comprising complexes of the invention in combination with dexamethasone. Preferably, the leukemia is chronic myeloid leukemia (CML), the HSP complexes comprises hsp70-peptide complexes, and the therapeutic modality is imatinib mesylate or Gleevec™.

In another embodiment, melanoma can be treated with a pharmaceutical composition comprising complexes of the invention in combination with dacarbazine.

In another embodiment, colorectal cancer can be treated with a pharmaceutical composition comprising complexes of the invention in combination with irinotecan.

In another embodiment, lung cancer can be treated with a pharmaceutical composition comprising complexes of the invention in combination with paclitaxel, docetaxel, etoposide and/or cisplatin.

In another embodiment, non-Hodgkin's lymphoma can be treated with a pharmaceutical composition comprising complexes of the invention in combination with cyclophosphamide, CHOP, etoposide, bleomycin, mitoxantrone and/or cisplatin.

In another embodiment, gastric cancer can be treated with a pharmaceutical composition comprising complexes of the invention in combination with cisplatin.

In another embodiment, pancreatic cancer can be treated with a pharmaceutical composition comprising complexes of the invention in combination with gemcitabine.

According to the invention, the complexes of the invention can be administered prior to, subsequently, or concurrently with anti-cancer agent(s), for the prevention or treatment of cancer. Depending on the type of cancer, the subject's history and condition, and the anti-cancer agent(s) of choice, the use of the complexes of the invention can be coordinated with the dosage and timing of chemotherapy.

The use of the complexes of the invention can be added to a regimen of chemotherapy. In one embodiment, the chemotherapeutic agent is gemcitabine at a dose ranging from 100 to 1000 $mg/m^2/cycle$. In one embodiment, the chemotherapeutic agent is dacarbazine at a dose ranging from 200 to 4000 $mg/m^2/cycle$. In a preferred embodiment, the dose of dacarbazine ranges from 700 to 1000 $mg/m^2/cycle$. In another embodiment, the chemotherapeutic agent is fludarabine at a dose ranging from 25 to 50 $mg/m^2/cycle$. In another embodiment, the chemotherapeutic agent is cytosine arabinoside (Ara-C) at a dose ranging from 200 to 2000 $mg/m^2/cycle$. In another embodiment, the chemotherapeutic agent is docetaxel at a dose ranging from 1.5 to 7.5 mg/kg/cycle. In another embodiment, the chemotherapeutic agent is paclitaxel at a dose ranging from 5 to 15 mg/kg/cycle. In yet another embodiment, the chemotherapeutic agent is cisplatin at a dose ranging from 5 to 20 mg/kg/cycle. In yet another embodiment, the chemotherapeutic agent is 5-fluorouracil at a dose ranging from 5 to 20 mg/kg/cycle. In yet another embodiment, the chemotherapeutic agent is doxorubicin at a dose ranging from 2 to 8 mg/kg/cycle. In yet another embodiment, the chemotherapeutic agent is epipodophyllotoxin at a dose ranging from 40 to 160 mg/kg/cycle. In yet another embodiment, the chemotherapeutic agent is cyclophosphamide at a dose ranging from 50 to 200 mg/kg/cycle. In yet another embodiment, the chemotherapeutic agent is irinotecan at a dose ranging from 50 to 75, 75 to 100, 100 to 125, or 125 to 150 $mg/m^2/cycle$. In yet another embodiment, the chemotherapeutic agent is vinblastine at a dose ranging from 3.7 to 5.4, 5.5 to 7.4, 7.5 to 11, or 11 to 18.5 $mg/m^2/cycle$. In yet another embodiment, the chemotherapeutic agent is vincristine at a dose ranging from 0.7 to 1.4, or 1.5 to 2 $mg/m^2/cycle$. In yet another embodiment, the chemotherapeutic agent is methotrexate at a dose ranging from 3.3 to 5, 5 to 10, 10 to 100, or 100 to 1000 $mg/m^2/cycle$.

In a preferred embodiment, the invention further encompasses the use of low doses of chemotherapeutic agents when administered as part of the combination therapy regimen. For example, initial treatment with the complexes of the invention increases the sensitivity of a tumor to subsequent challenge with a dose of chemotherapeutic agent, which dose is near or below the lower range of dosages when the chemotherapeutic agent is administered without complexes of the invention.

In one embodiment, complexes of the invention and a low dose (e.g., 6 to 60 mg/m$^2$/day or less) of docetaxel are administered to a cancer patient. In another embodiment, complexes of the invention and a low dose (e.g., 10 to 135 mg/m$^2$/day or less) of paclitaxel are administered to a cancer patient. In yet another embodiment, complexes of the invention and a low dose (e.g., 2.5 to 25 mg/m$^2$/day or less) of fludarabine are administered to a cancer patient. In yet another embodiment, complexes of the invention and a low dose (e.g., 0.5 to 1.5 g/m$^2$/day or less) of cytosine arabinoside (Ara-C) are administered to a cancer patient. In another embodiment, the chemotherapeutic agent is gemcitabine at a dose ranging from 10 to 100 mg/m$^2$/cycle. In another embodiment, the chemotherapeutic agent is cisplatin, e.g., PLATINOL or PLATINOL-AQ (Bristol Myers), at a dose ranging from 5 to 10, 10 to 20, 20 to 40, or 40 to 75 mg/m$^2$/cycle. In yet another embodiment, a dose of cisplatin ranging from 7.5 to 75 mg/m$^2$/cycle is administered to a patient with ovarian cancer. In yet another embodiment, a dose of cisplatin ranging from 5 to 50 mg/m$^2$/cycle is administered to a patient with bladder cancer. In yet another embodiment, the chemotherapeutic agent is carboplatin, e.g., PARAPLATIN (Bristol Myers), at a dose ranging from 2 to 4, 4 to 8, 8 to 16, 16 to 35, or 35 to 75 mg/m$^2$/cycle. In yet another embodiment, a dose of carboplatin ranging from 7.5 to 75 mg/m$^2$/cycle is administered to a patient with ovarian cancer. In another embodiment, a dose of carboplatin ranging from 5 to 50 mg/m$^2$/cycle is administered to a patient with bladder cancer. In yet another embodiment, a dose of carboplatin ranging from 2 to 20 mg/m$^2$/cycle is administered to a patient with testicular cancer. In yet another embodiment, the chemotherapeutic agent is docetaxel, e.g., TAXOTERE (Rhone Poulenc Rorer) at a dose ranging from 6 to 10, 10 to 30, or 30 to 60 mg/m$^2$/cycle. In yet another embodiment, the chemotherapeutic agent is paclitaxel, e.g., TAXOL (Bristol Myers Squibb), at a dose ranging from 10 to 20, 20 to 40, 40 to 70, or 70 to 135 mg/kg/cycle. In yet another embodiment, the chemotherapeutic agent is 5-fluorouracil at a dose ranging from 0.5 to 5 mg/kg/cycle. In yet another embodiment, the chemotherapeutic agent is doxorubicin, e.g., ADRIAMYCIN (Pharmacia & Upjohn), DOXIL (Alza), RUBEX (Bristol Myers Squibb), at a dose ranging from 2 to 4, 4 to 8, 8 to 15, 15 to 30, or 30 to 60 mg/kg/cycle.

In another embodiment, complexes of the invention is administered in combination with one or more anti-angiogenic agents, which includes, but is not limited to, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077-2083), a 14-amino acid peptide corresponding to a fragment of collagen I (Tolma et al., 1993, J. Cell Biol. 122:497-511), a 19 amino acid peptide corresponding to a fragment of Thrombospondin I (Tolsma et al., 1993, J. Cell Biol. 122:497-511), a 20-amino acid peptide corresponding to a fragment of SPARC (Sage et al., 1995, J. Cell. Biochem. 57:1329-1334), or any fragments, family members, or variants thereof, including pharmaceutically acceptable salts thereof.

Other peptides that inhibit angiogenesis and correspond to fragments of laminin, fibronectin, procollagen, and EGF have also been described (see, e.g., Cao, 1998, Prog Mol Subcell Biol. 20:161-176). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569-571; Hammes et al., 1996, Nature Medicine 2:529-533). Moreover, inhibition of the urokinase plasminogen activator receptor by receptor antagonists inhibits angiogenesis, tumor growth and metastasis (Min et al., 1996, Cancer Res. 56: 2428-33; Crowley et al., 1993, Proc Natl Acad. Sci. 90:5021-25). Use of such anti-angiogenic agents in combination with the complexes is also contemplated by the present invention.

In yet another embodiment, complexes of the invention is used in association with a hormonal treatment. Hormonal therapeutic treatments comprise hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), and antiandrogens (e.g. cyproterone acetate).

In yet another embodiment, complexes of the invention are used in association with a gene therapy program in the treatment of cancer. In one embodiment, gene therapy with recombinant cells secreting interleukin-2 is administered in combination with complexes of the invention to prevent or treat cancer, particularly breast cancer (See, e.g., Deshmukh et al., 2001, J. Neurosurg. 94:287-92). In other embodiments, gene therapy is conducted with the use of polynucleotide compounds, such as but not limited to antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, many are oncogenes, growth factor genes, growth factor receptor genes, cell cycle genes, DNA repair genes, and are well known in the art.

In another embodiment, complexes of the invention is administered in conjunction with a regimen of radiation therapy. For radiation treatment, the radiation can be gamma rays or X-rays. The methods encompass treatment of cancer comprising radiation therapy, such as external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J.B. Lippencott Company, Philadelphia. In preferred embodiments, the radiation treatment is administered as external beam radiation or teletherapy wherein the radiation is directed from a remote source. In various preferred embodiments, the radiation treatment is administered as internal therapy or brachytherapy wherein a radioactive source is placed inside the body close to cancer cells or a tumor mass. Also encompassed is the combined use of complexes of the invention with photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments, complexes of the invention is administered, in combination with at least one chemotherapeutic agent, for a short treatment cycle to a cancer patient to treat cancer. The duration of treatment with the chemotherapeutic agent may vary according to the particular cancer therapeutic agent used. The invention also contemplates discontinuous administration or daily doses divided into several partial administrations. An appropriate treatment time for a particular cancer therapeutic agent will be appreciated by the skilled artisan, and the invention contemplates the continued assessment of optimal treatment schedules for each cancer therapeutic agent. The present invention contemplates at least one cycle, preferably more than one cycle during which a single therapeutic or sequence of therapeutics is administered. An appropriate period of time for one cycle will be appreciated by the skilled artisan, as will the total number of cycles, and the interval between cycles.

In another embodiment, complexes of the invention are used in combination with compounds that ameliorate the symptoms of the cancer (such as but not limited to pain) and the side effects produced by the complexes of the invention (such as but not limited to flu-like symptoms, fever, etc.). Accordingly, many compounds known to reduce pain, flu-like symptoms, and fever can be used in combination or in admixture with complexes of the invention. Such compounds include analgesics (e.g, acetaminophen), decongestants (e.g., pseudoephedrine), antihistamines (e.g., chlorpheniramine maleate), and cough suppressants (e.g., dextromethorphan).

5.5. Target Infectious Diseases

Infectious diseases that can be treated or prevented by the methods of the present invention are caused by infectious agents including, but not limited to, viruses, bacteria, fungi protozoa, helminths, and parasites. The invention is not limited to treating or preventing infectious diseases caused by intracellular or extracellular pathogens. Combination therapy encompasses in addition to the administration of pharmaceutical compositions of the invention, the uses of one or more modalities that aid in the prevention or treatment of infectious diseases, which modalities include, but is not limited to antibiotics, antivirals, antiprotozoal compounds, antifungal compounds, and antihelminthics. Other treatment modalities that can be used to treat or prevent infectious diseases include immunotherapeutics, polynucleotides, antibodies, cytokines, and hormones as described above.

Infectious virus of both human and non-human vertebrates, include retroviruses, RNA viruses and DNA viruses. Examples of virus that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Retroviruses that are contemplated include both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retrovirises include Mason-Pfizer monkey virus (MPMV) and simian retrovirus type 1 (SRV-1). The complex retrovirises include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus. (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxyiridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A,B,C,D,E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents.

Many examples of antiviral compounds that can be used in combination with the complexes of the invention are known in the art and include but are not limited to: rifampicin, nucleoside reverse transcriptase inhibitors (e.g., AZT, ddI, ddC, 3TC, d4T), non-nucleoside reverse transcriptase inhibitors (e.g., Efavirenz, Nevirapine), protease inhibitors (e.g., aprenavir, indinavir, ritonavir, and saquinavir), idoxuridine, cidofovir, acyclovir, ganciclovir, zanamivir, amantadine, and Palivizumab. Other examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscamet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime.

Bacterial infections or diseases that can be treated or prevented by the methods of the present invention are caused by bacteria including, but not limited to, bacteria that have an intracellular stage in its life cycle, such as mycobacteria (e.g., *Mycobacteria tuberculosis, M. bovis, M. avium, M leprae*, or *M. africanum*), rickettsia, mycoplasma, chlamydia, and legionella. Other examples of bacterial infections contemplated include but are not limited to infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species. Specific examples of infectious bacteria include but are not limited to: *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus aecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneunmoniae, Pasturella multocida, Fusobacterium nucleatuin, Streptobacillus moniliformis, Treponema pallidum, Treponema pertenue, Leptospira, Rickettsia,* and *Actinoyyces israelli.*

Antibacterial agents or antibiotics that can be used in combination with the complexes of the invention include but are not limited to: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g. amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g. clindamycin, and lincomycin), macrolides (e.g., azithromycin, carbomycin, clarithromycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Additional examples of antibacterial agents include but are not limited to Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmnenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Inipenem; Isoconazole; Isepanicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide;

Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlinycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafingin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Fungal diseases that can be treated or prevented by the methods of the present invention include but not limited to aspergilliosis, crytococcosis, sporotrichosis, coccidioidomycosis, paracoccidioidomycosis, histoplasmosis, blastomycosis, zygomycosis, and candidiasis.

Antifungal compounds that can be used in combination with the complexes of the invention include but are not limited to: polyenes (e.g., amphotericin b, candicidin, mepartricin, natamycin, and nystatin), allylamines (e.g., butenafine, and naftifine), imidazoles (e.g., bifonazole, butoconazole, chlordantoin, flutrimazole, isoconazole, ketoconazole, and lanoconazole), thiocarbamates (e.g., tolciclate, tolindate, and tolnaftate), triazoles (e.g., fluconazole, itraconazole, saperconazole, and terconazole), bromosalicylchloranilide, buclosamide, calcium propionate, chlorphenesin, ciclopirox, azaserine, griseofulvin, oligomycins, neomycin undecylenate, pyrrolnitrin, siccanin, tubercidin, and viridin. Additional examples of antifungal compounds include but are not limited to Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofingin; Lydimycin; Mepartricin; Miconazole; Miconazole Nitrate; Monensin; Monensin Sodium; Naftifine Hydrochloride; Neomycin Undecylenate; Nifuratel; Nifinerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafuigin; Undecylenic Acid; Viridoflilvin; Zinc Undecylenate; and Zinoconazole Hydrochloride.

Parasitic diseases that can be treated or prevented by the methods of the present invention including, but not limited to, amebiasis, malaria, *leishmania*, coccidia, giardiasis, cryptosporidiosis, toxoplasmosis, and trypanosomiasis. Also encompassed are infections by various worms, such as but not limited to *ascariasis*, ancylostomiasis, trichuriasis, strongyloidiasis, toxoccariasis, trichinosis, onchocerciasis. filaria, and dirofilariasis. Also encompassed are infections by various flukes, such as but not limited to schistosomiasis, paragonimiasis, and clonorchiasis. Parasites that cause these diseases can be classified based on whether they are intracellular or extracellular. An "intracellular parasite" as used herein is a parasite whose entire life cycle is intracellular. Examples of human intracellular parasites include *Leishmania* spp., *Plasmodium* spp., *Trypanosoma cruzi, Toxoplasma gondii, Babesia* spp., and *Trichinella spiralis*. An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites". These parasites may exist most of their lives or only a small portion of their lives in an extracellular environment, but they all have at least one obligate intracellular stage in their life cycles. This latter category of parasites includes *Trypanosoma rhodesiense* and *Trypanosoina gambienise, Isospora* spp., *Cryptosporidium* spp, *Eimeria* spp., *Neospora* spp., *Sarcocystis* spp., and *Schistosoma* spp.

Many examples of antiprotozoal compounds that can be used in combination with the complexes of the invention to treat parasitic diseases are known in the art and include but are not limited to: quinines, chloroquine, mefloquine, proguanil, pyrimethamine, metronidazole, diloxanide furoate, tinidazole, amphotericin, sodium stibogluconate, trimoxazole, and pentamidine isetionate. Many examples of antiparasite drugs that can be used in combination with the complexes of the invention to treat parasitic diseases are known in the art and include but are not limited to: mebendazole, levamisole, niclosamide, praziquantel, albendazole, ivermectin, diethylcarbamazine, and thiabendazole. Further examples of antiparasitic compounds include but are not limited to Acedapsone; Amodiaquine Hydrochloride; Amquinate; Arteflene; Chloroquine; Chloroquine Hydrochloride; Chloroquine Phosphate; Cycloguanil Pamoate; Enpiroline Phosphate; Halofantrine Hydrochloride; Hydroxychloroquine Sulfate;

Mefloquine Hydrochloride; Menoctone; Mirincamycin Hydrochloride; Primaquine Phosphate; Pyrimethamine; Quinine Sulfate; and Tebuquine.

In some embodiments, antibodies can be used for treatment and/or prevention of infectious disease. In a less preferred embodiment, the complexes of the invention can be used in combination with a non-α2M-based vaccine composition. Examples of such vaccines for humans are described in The Jordan Report 2000, Accelerated Development of Vaccines, National Institute of Health, which is incorporated herein by reference in its entirety. Many vaccines for the treatment of non-human vertebrates are disclosed in Bennett, K. Compendium of Veterinary Products, 3rd ed. North American Compendiums, Inc., 1995, which is incorporated herein by reference in its entirety.

5.6. Therapeutic Regimens

For any of the combination therapies described above for treatment or prevention of cancer and infectious diseases, the pharmaceutical compositions of the invention can be administered prior to, concurrently with, or subsequent to the administration of the combined modality. The combined modality can be any one of the modalities described above for treatment or prevention of cancer or infectious disease.

In one embodiment, the pharmaceutical composition of the invention is administered to a subject at reasonably the same time as the other modality. This method provides that the two administrations are performed within a time frame of less than one minute to about five minutes, or up to about sixty minutes from each other, for example, at the same doctor's visit.

In another embodiment, the pharmaceutical compositions of the invention and a combined modality are administered at exactly the same time. In yet another embodiment the pharmaceutical compositions of the invention and the combined modality are administered in a sequence and within a time interval such that the pharmaceutical compositions of the invention and the modality can act together to provide an increased benefit than if they were administered alone. In another embodiment, the pharmaceutical compositions of the invention and a combined modality are administered sufficiently close in time so as to provide the desired therapeutic or prophylactic outcome. Each can be administered simultaneously or separately, in any appropriate form and by any suitable route. In one embodiment, the pharmaceutical compositions of the invention and the modality are administered by different routes of administration. In an alternate embodiment, each is administered by the same route of administration. The pharmaceutical compositions of the invention can be administered at the same or different sites, e.g. arm and leg. When administered simultaneously, the pharmaceutical compositions of the invention and the combined modality may or may not be administered in admixture or at the same site of administration by the same route of administration.

In various embodiments, the complexes of the invention and the combined modality are administered less than 1 hour apart, at about 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In other embodiments, the pharmaceutical compositions of the invention and vaccine composition are administered 2 to 4 days apart, 4 to 6 days apart, 1 week a part, 1 to 2 weeks apart, 2 to 4 weeks apart, one moth apart, 1 to 2 months apart, or 2 or more months apart. In preferred embodiments, the complexes of the invention and the combined modality are administered in a time frame where both are still active. One skilled in the art would be able to determine such a time frame by determining the half life of each administered component.

In one embodiment, the pharmaceutical composition of the invention and the combined modality are administered within the same patient visit. In a specific preferred embodiment, the pharmaceutical compositions of the invention is administered prior to the administration of the modality. In an alternate specific embodiment, the pharmaceutical compositions of the invention is administered subsequent to the administration of the modality.

In certain embodiments, the pharmaceutical composition of the invention and the modality are cyclically administered to a subject. Cycling therapy involves the administration of the pharmaceutical compositions of the invention for a period of time, followed by the administration of a modality for a period of time and repeating this sequential administration. Cycling therapy can reduce the development of resistance to one or more of the therapies, avoid or reduce the side effects of one of the therapies, and/or improve the efficacy of the treatment. In such embodiments, the invention contemplates the alternating administration of a pharmaceutical compositions of the invention followed by the administration of a modality 4 to 6 days later, preferable 2 to 4 days, later, more preferably 1 to 2 days later, wherein such a cycle may be repeated as many times as desired. In certain embodiments, the pharmaceutical compositions of the invention and the modality are alternately administered in a cycle of less than 3 weeks, once every two weeks, once every 10 days or once every week. In certain embodiments, a patient is administered the composition of the invention about every 1, 2, 3, 4, 5, 6, 7, 8, 9, or 10 days.

In a specific embodiment, pharmaceutical compositions of the invention are administered to a subject within a time frame of one hour to twenty four hours after the administration of a modality. The time frame can be extended further to a few days or more if a slow- or continuous-release type of modality delivery system is used. In certain embodiments, the pharmaceutical compositions of the invention are administered to a subject periodically as described above, for throughout the remainder of the patients life.

5.7. CD91 Activity Assays

After its purification, an α2-M-antigenic molecule complex can be further characterized to measure its effect on CD91 activity and the CD91 signaling pathway. For example, the α2M-antigenic molecule complex may be characterized by testing its effect on CD91 cellular activity. Such assays include downstream signaling assays, antigen presentation assays, assays for antigen-specific activation of cytotoxic T cells, and the like. Such assays can be used to test and/or measure of an immune response.

In various embodiments, a α2M complex may be tested for its effect on innate CD91 signaling activity. For example, downstream signaling effects of CD91 activation which can be assayed include, but are not limited to: enhanced locomotion and chemotaxis of macrophages (Forrester et al., 1983, Immunology 50: 251-259), down regulation of proteinase synthesis, and elevation of intracellular calcium, inositol phosphates and cyclic AMP (Misra et al., 1993, Biochem. J., 290:885-891). Other innate immune responses that can be tested are release of cytokines (i.e., IL-12, IL1β, GMCSF, and TNFα).

For example, in one embodiment, a chemotaxis assay can be used to further characterize a candidate α2M complex isolated from the serum of a mammal. It is known that α2M modified by protease interaction can induce directional migration of cells towards their ligand. A number of techniques can be used to test chemotactic migration in vitro (see, e.g., Leonard et al., 1995, "Measurement of α and β Chemokines", in Current Protocols in Immunology, 6.12.1-6.12.28, Ed. Coligan et al., John Wiley & Sons, Inc. 1995). For example, in one embodiment, a candidate compound can be tested for its ability to modulate the ability of α2MR to induce migration of cells that express the receptor using a chemokine gradient in a multiwell Boyden chemotaxis chamber. In a specific example of this method, a serial dilution of a α2M complex identified in the primary screen is placed in the bottom wells of the Boyden chemotaxis chamber. A constant amount of ligand is also added to the dilution series. As a control, at least one aliquot contains only ligand (e.g., α2M). The contribution of the α2M complex to the chemotactic activity of α2MR is measured by comparing number of migrating cells on the lower surface of the membrane filter of the aliquots containing only ligand (e.g., α2M), with the number of cells in aliquots containing α2M polypeptide and ligand (e.g., α2M). If addition of the α2M complex to the ligand (e.g., α2M) solution results in a decrease in the number of cells detected the membrane relative to the number of cells detected using a solution containing only ligand (e.g., α2M), then an antagonist of ligand (e.g., α2M) induction of chemotactic activity of α2MR-expressing cells is identified.

Elevation in intracellular ionized calcium concentration ($[Ca^{2+}]_i$) is also an indicator of α2MR activation (Misra et al., 1993, supra). Thus, in another embodiment, calcium flux assays can be used as secondary screens to further characterize the effects of α2M complex. Intracellular calcium ion concentration can be measured in cells that express the CD91 in the presence of the ligand, in the presence and the absence of a α2M complex. For example, calcium mobilization can be detected and measured by flow cytometry, by labeling with fluorescent dyes that are trapped intracellularly A fluorescent dye such as Indo-1 exhibits a change in emission spectrum upon binding calcium, the ratio of fluorescence produced by the calcium-bound dye to that produce by the unbound dye may be used to estimate the intracellular calcium concentration. In a specific embodiment, cells are incubated in a cuvette in media containing Indo-1 at 37_C and are excited, and fluorescence is measured using a fluorimeter (Photon Technology Corporation, International). The ligand is added at a specific time point, in the presence and the absence of a α2M complex, EGTA is added to the cuvette to release and chelate total calcium, and the response is measured. Binding of ligand results in increased intracellular $Ca^{2+}$ concentration in cells that express α2MR. An agonist results in a relative increased intracellular $Ca^{2+}$ concentration, whereas an antagonist results in a relative decreased intracellular $Ca^{2+}$ concentration In other embodiments, to detect or measure the activity of α2M-antigenic molecule complexes, an antigen presentation assay may be performed to predict how effective an α2M-antigenic molecule complexes will be in vivo.

Such re-presentation assays are known in the art, and have been described previously (Suto and Srivastava, 1995, Science 269:1585-1588). For example, in one embodiment, antigen presenting cells, such as a macrophage cell line (e.g., RAW264.7), are mixed with antigen-specific T cells in media, using approximately 10,000 cells of each type at approximately a 1:1 ratio. Complexes of α2M and a peptide antigen, is added to the cells and the culture is incubated for approximately 20 hours. In one embodiment an IFN-γ release assay may be used to measure or detect a T cell response. After washing, cells are fixed, permeabilized, and reacted with dye-labeled antibodies reactive with human IFN-γ (PE-anti-IFN-γ). Samples are analyzed by flow cytometry using standard techniques. Alternatively, a filter immunoassay, ELISA (enzyme linked immunosorbent assay), or enzyme-linked immunospot assay (ELISPOT) assay, may be used to detect specific cytokines produced by an activated T cell. In one embodiment, for example, a nitrocellulose-backed microtiter plate is coated with a purified cytokine-specific primary antibody, i.e., anti-IFN-γ, and the plate is blocked to avoid background due to nonspecific binding of other proteins. A sample of APC cells stimulated with antigen is diluted onto the wells of the microtiter plate. A labeled, e.g., biotin-labeled, secondary anti-cytokine antibody is added. The antibody cytokine complex can then be detected, i.e., by enzyme-conjugated streptavidin-cytokine-secreting cells will appear as "spots" by visual, microscopic, or electronic detection methods. In another embodiment, "tetramer staining" assay (Altman et al., 1996, Science 274: 94-96) may be used to identify antigen-specific T-cells. For example, an MHC molecule containing a specific peptide antigen, is multimerized to make soluble peptide tetramers and labeled, for example, by complexing to streptavidin. The MHC-peptide antigen complex is then mixed with a population of stimulated T cells. Biotin is then used to stain T cells which recognize and bind to the MHC-antigen complex.

5.8. Induction of Tumor Cell Necrosis

In certain embodiments of the invention it can be advantageous to induce tumor necrosis in a mammal prior to isolating alpha (2) macroglobulin-antigenic molecule complexes from the animal. Applicants have demonstrated that induction of tumor necrosis prior to isolation of complexes can enhance the effectiveness of complexes in treatment and prevention of cancer. See Section 6 Example results. Applicants believe, without limiting themselves to any one theory, that necrotic tumor cells shed antigens specific to the tumor. The shed antigenic molecules then enter bodily fluid such as blood and form complexes with alpha (2) macroglobulin.

Numerous methods can be used to induce tumor necrosis. The administration of agents that induce tumor cell necrosis is common in cancer therapy. Examples of tumor-necrosis agents include but are not limited to bleach, cisplatin/epinephrine injectable gel (Vogl et al., 2002, British Journal of Cancer 86(4):524-529), ONO-4007 a synthetic analog of lipid A (Satoh et al., 2002, Cancer Immunol. Immunother 50(12):653-662), tumor necrosis factor (TNF), soluble ethanol (Burgener et al., 1987, Invest Radiol. 22(6):472-478), antibody against epidermal growth factor receptor (alpha EGFr) (Wersall et al., 1997, Cancer Immunol. Immunother. 44(3):157-164), OK-432 a penicillin-treated freeze-dried *Streptococcus* (Ishiko et al., 1997 Int. J. Immunopharmacol. 19(7):405-412), adenovirus (ONYX-015) (Ganly et al., 2000, Clin. Cancer Res. 6(3):798-806), IL4-PE chimeric protein (Rand et al., 2000, Clin. Cancer Res. 6(6):2157-2165), nimustine (ACNU) (Wakabayashi et al., 2001, 18(1):23-28).

Tumor necrosis can also be achieved with other methods such as but not limited to photosensitization of tumor involving photodynamic therapy with hypercin (Blank et al., 2001, Oncol. Res. 12 (9-10:409-418)), selective microwave irradiation of tissue as described in U.S. Pat. No. 6,131,577, application of heat to tumor tissue to induce necrosis as described in U.S. Pat. No. 5,928,159, laser heating of sub-surface flesh as described in U.S. Pat. No. 5,897,549, transurethral focused ultrasound therapy for causing necrosis of prostate tumor tissues as described in U.S. Pat. Nos. 5,895,356 and 5,843,144, silver nitrate and dextran paste used in uterine cancers to achieve necrosis of body cavity lining as described in U.S. Pat. No. 5,891,457, pulsed magnetic radiation as described in U.S. Pat. No. 5,776,175, non-ionizing radiation as described in U.S. Pat. No. 5,527,352, catheter with heating means as described in U.S. Pat. No. 5,492,529, endoscopic guidance of laser energy as described in U.S. Pat. No. 5,487,740, devices with electrodes for heating selective tissue as described in U.S. Pat. Nos. 5,318,564, 4,186,729 and 4,237,898, radio frequency thermotherapy as described in U.S. Pat. Nos. 5,186,181, 4,154,246, 4,119,102, 3,991,770 and 4,230,129, a heatable inflatable device for treating internal tissue lining as described in U.S. Pat. No. 5,159,925, immunopotentiating compositions such as described in U.S. Pat. No. 5,149,527, injection of ferromagnetic particles near tumor tissue as described in U.S. Pat. Nos. 4,983,159, 4,392,040, and 4,545,368, catheter application of heat and radiation to tissues as described in U.S. Pat. No. 4,763,671, and treatment of tissues with a liquified-gas cooling medium as described in U.S. Pat. No. 3,674,031.

In certain embodiments, induction of necrosis may be between one hour and two months prior to isolation of alpha (2) macroglobulin complexes. In specific embodiments, induction may be for 1 hour, 12 hours, 1 day, 3 days, 1 week, 3 weeks, 5 weeks, 1 month or 2 months prior to isolation of alpha (2) macroglobulin complexes. Induction of necrosis may be repeated, as necessary, as would be understood by the skilled practitioner.

In certain embodiments, chemotherapeutic agents are administered to the patient prior to isolation of the alpha (2) macroglobulin-antigenic molecule complexes. In such embodiments, chemotherapeutic agents such as those described above in Section 5.4 can be used.

The references describing induction of tumor necrosis above are incorporated by reference herein in their entirety.

5.9. Dosage Regimens and Formulation

Covalent or noncovalent complexes of α2M polypeptides and antigenic molecules of the invention may be formulated into pharmaceutical preparations for administration to mammals for treatment or prevention of cancer or infectious diseases at therapeutically effective doses for immunotherapy. Drug solubility and the site of absorption are factors which should be considered when choosing the route of administration of a therapeutic agent.

Toxicity and therapeutic efficacy of such compositions comprising α2M complexes can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Alpha (2) macroglobulin complexes that exhibit large therapeutic indices are preferred. While compounds that exhibit toxic side effects may be used, care should be taken to design a delivery system that targets such compositions comprising $α_2M$ complexes to the site of affected tissue in order to minimize potential damage to uninfected cells and, thereby, reduce side effects.

The subject or patient receiving the treatment is preferably a mammal including, but not limited to, domestic animals, such as cats and dogs; wild animals, including foxes and raccoons; livestock and fowl, including horses, cattle, sheep, turkeys and chickens, as well as any rodents. Most preferably, the subject is human.

The data obtained from the cell culture assays and animal studies can be used in formulating a range of dosage for use in humans. The dosage of such compositions comprising α2M complexes lies preferably within a range of circulating concentrations that include the $ED_{50}$ with little or no toxicity. The dosage may vary within this range depending upon the dosage form employed and the route of administration utilized. For any compositions comprising α2M complexes used in the method of the invention, the therapeutically effective dose can be estimated initially from cell culture assays. A dose may be formulated in animal models to achieve a circulating plasma concentration range that includes the $IC_{50}$ (i.e., the concentration of the compositions comprising α2M complex that achieves a half-maximal inhibition of symptoms) as determined in cell culture. Such information can be used to more accurately determine useful doses in humans. Levels in plasma may be measured, for example, by high performance liquid chromatography.

Selection of the preferred effective dose will be determined by a skilled artisan based upon considering several factors which will be known to one of ordinary skill in the art. Such factors include the particular form of compositions comprising α2M complexes, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

Alpha (2) macroglobulin complexes of the invention may optionally be administered with one or more adjuvants in order to enhance the immunological response. For example, depending on the host species, adjuvants which may be used include, but are not limited to: mineral salts or mineral gels such as aluminum hydroxide, aluminum phosphate, and calcium phosphate; surface active substances such as lysolecithin, pluronic polyols, polyanions, peptides, oil emulsions, keyhole limpet hemocyanins, and dinitrophenol; immunostimulatory molecules, such as cytokines, saponins (e.g., QS-21), muramyl dipeptides and tripeptide derivatives, CpG dinucleotides, CpG oligonucleotides, monophosphoryl Lipid A, and polyphosphazenes; particulate and microparticulate adjuvant, such as emulsions, liposomes, virosomes, cochleates; or an immune stimulating complex mucosal adjuvants, Freund's (complete and incomplete, and potentially useful human adjuvants such as BCG (bacille Calmette-Guerin) and *corynebacterium parvum*.). Furthermore, the following patents and printed publications disclose immunostimulatory oligonucleotides which include CpG oligonucleotides that can be used in the compositions of the invention: U.S. Pat. Nos. 6,207,646; 6,339,068; 6,239,116; 6,429,199; and PCT Patent publication, WO 01/22972, WO 00/06588, by Krieg et al.; WO 01/83503; WO 01/55370; and WO 01/12804 by Agrawal; WO 02/052002 by Fearon et al.; WO 01/35991 by Tuck et al.; WO 01/12223 by Van Nest; WO 98/55495; WO 99/62923 by Schwartz; U.S. Pat. No. 6,406,705 by Davis et al.; and PCT Patent publication WO 02/26757 by Kandimalla et al., all of the forgoing are incorporated herein by reference in their entireties. Other suitable adjuvants that can be used in the invention can be found in A Compendium of Vaccine Adjuvants and Excipients (2nd Edition), Vogel, F., Powell, M., and Alving, C., in Vaccine Design—The Subunit and Adjuvant Approach, Powell, M., Newman, M., Burdman, J., Editors, Plenum Press, New York, 1995, pp. 141-227, and 2nd Meeting on Novel Adjuvants Currently In/Close to Human Clinical Testing, World Health Organization—Organization Mondiale de la Sante Foundation Merieux, Annecy, France, 5-7 June 2000, Kenney, R., Rabinovich, N. R., Pichyangkul, S., Price, V., and Engers, H., Vaccine, 20 (2002) 2155-63. All of which are incorporated herein by reference.

Alpha (2) macroglobulin complexes of the invention may be administered using any desired route of administration, including but not limited to, e.g., subcutaneously, intravenously or intramuscularly, although intradermally or mucosally is preferred. Advantages of intradermal or mucosal administration include use of lower doses and rapid absorption, respectively. Mucosal routes of administration include, but are not limited to, oral, rectal and nasal administration. Preparations for mucosal administrations are suitable in various formulations as described below. The route of administration can be varied during a course of treatment.

The doses recited above are preferably given once weekly for a period of about 4-6 weeks, and the mode or site of administration is preferably varied with each administration. In a preferred example, subcutaneous administrations are given, with each site of administration varied sequentially. Thus, by way of example and not limitation, the first injection may be given subcutaneously on the left arm, the second on the right arm, the third on the left belly, the fourth on the right belly, the fifth on the left thigh, the sixth on the right thigh, etc. The same site may be repeated after a gap of one or more injections. Also, split injections may be given. Thus, for example, half the dose may be given in one site and the other half on an other site on the same day.

Alternatively, the mode of administration is sequentially varied, e.g., weekly injections are given in sequence subcutaneously, intramuscularly, intravenously or intraperitoneally.

After 4-6 weeks, further injections are preferably given at two-week intervals over a period of time of one or more months. Later injections may be given monthly. The pace of later injections may be modified, depending upon the patient's clinical progress and responsiveness to the immunotherapy.

Pharmaceutical compositions for use in accordance with the present invention may be formulated in conventional manner using one or more physiologically acceptable carriers or excipients.

Compositions comprising covalent or noncovalent compositions comprising α2M complexes formulated in a compatible pharmaceutical carrier may be prepared, packaged, and labeled for treatment of the indicated cancer or infectious disease. In preferred aspects, an amount of a composition comprising α2M complex is administered to a human that is in the range of about 1 µg to 5 mg, preferably 10 to 200 µg, preferably 10, 20, 25, 50, 100, or 200 µg. In a preferred embodiment, the composition of the invention comprising α2M complex is given once weekly for about 4-6 weeks, intradermally with the site of administration varied sequentially. In a preferred embodiment, the composition of a invention comprising α2M complex is given as primary treatment or twelve hours to one week after the diseased tissue is treated in vivo to induce tissue necrosis.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the covalent or noncovalent and/or α2M complexes and their physiologically acceptable solvates may be formulated for administration by inhalation or insufflation (either through the mouth or the nose) or oral, buccal, parenteral, rectal administration or, in the case of tumors, directly injected into a solid tumor.

In a preferred embodiment, the composition of the invention comprising alpha (2) macroglobulin further comprises 9% sucrose, 5-10 mM potassium phosphate. In a related preferred embodiment, the pH of the composition of the invention is 7.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the compositions comprising α2M complexes. Such compositions may take the form of tablets or lozenges formulated in conventional manner.

For administration by inhalation, the compositions comprising α2M complexes may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compositions comprising α2M complexes and a suitable powder base such as lactose or starch.

The compositions comprising α2M complexes may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions comprising α2M complexes may also be formulated in rectal compositions such as suppositories or retention enemas, e.g., containing conventional suppository bases such as cocoa butter or other glycerides.

In addition to the formulations described previously, the compositions comprising α2M complexes may also be formulated as a depot preparation. Such long acting formulations may be administered by implantation (for example, subcutaneously or intramuscularly) or by intramuscular injection. Thus, for example, the compositions comprising α2M complexes may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions comprising α2M complexes may, if desired, be presented in a pack or dispenser device which may contain one or more unit dosage forms containing the covalent or noncovalent complexes of α2M and antigenic molecules. The pack may for example comprise metal or plastic foil, such as a blister pack. The pack or dispenser device may be accompanied by instructions for administration.

5.10. Determination of Vaccine Efficacy

The immunopotency of the compositions of the invention can be determined by monitoring the immune response in test animals following immunization with the compositions of the invention, or by use of any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects. Methods of introducing the vaccine may include oral, intracerebral, intradermal, transdermal, intramuscular, intraperitoneal, intravenous, subcutaneous, intranasal or any other standard routes of immunization. The immune response of the test subjects can be analyzed by various approaches such as: the reactivity of the resultant immune serum to the antigen of interest, as assayed by known techniques, e.g., ELISA (enzyme-linked immunosorbent assay), immunoblots, radioimmunoprecipitations, etc., or by protection of the immunized host against cancer or the infectious disease.

As one example of suitable animal testing of a vaccine protective a disease, the vaccine of the invention may be tested in rabbits for the ability to induce an antibody response to the antigenic molecule. Male specific-pathogen-free (SPF) young adult New Zealand White rabbits may be used. The test group each receives a fixed concentration of the vaccine. A control group receives an injection of 1 mM Tris-HCl pH 9.0 without the antigen molecule. Blood samples may be drawn from the rabbits every one or two weeks, and serum analyzed for antibodies to the antigenic molecule. The presence of antibodies specific for the antigen may be assayed, e.g., using an ELISA assay.

5.11. Kits

The invention also provides kits for carrying out the therapeutic regimens of the invention. Such kits comprise in one or more containers therapeutically or prophylactically effective amounts of the covalent or noncovalent α2M complexes in pharmaceutically acceptable form. The α2M complexes in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of α2M complexes by a clinician or by the patient.

6. EXAMPLE

Suppression and Reduction of Tumors

The following results show that alpha (2) macroglobulin complexes can be purified intact from the serum of tumor-bearing animals and used to protect against cancer. Inbred mice were used as a model to examine the effect of immunization with alpha (2) macroglobulin complexed to antigenic molecules derived from tumors on a subsequent challenge with live tumor cells. The results presented below support the claimed invention particularly the effectiveness of autologous therapies comprising administration of alpha (2) macroglobulin complexes isolated from a mammal having a tumor. The immune systems of the inbred mice used are identical or nearly so, such that the results can be extrapolated to autologous therapies for treatment of cancer.

Materials and Methods

To purify alpha (2) macroglobulin-antigenic molecule complexes, serum from mice was diluted 1:1 with 0.04 M Tris pH 7.6, 0.15 M NaCl. The mixture was then applied to a 65 ml Sephacryl S 300R (Sigma) column equilibrated and eluted with the same buffer. A 65 ml column is used for about 10 ml of serum. Alpha (2) macroglobulin-positive fractions are determined by dot blot and the buffer changed to a 0.01 M sodium phosphate buffer at pH 7.5 by use of a PD-10 column. Alternatively, the 0.01 M sodium phosphate buffer at pH 7.5 can be used as buffer in the 65 ml column to eliminate the step of exchanging the buffer. The complex-containing fractions were applied to a Concanavalin A sepharose column. Bound complexes are eluted with 0.2 M methylmannose pyranoside, or 5% methylmannose pyranoside, and applied to a PD-10 column to change the buffer to 0.05 M sodium acetate buffer pH 6.0, and applied to a DEAE column equilibrated with 0.05 M sodium acetate buffer pH 6.0. Alpha (2) macroglobulin was eluted with 0.13 M sodium acetate buffer in a pure form, as analyzed by SDS-PAGE and immunoblotting.

In some experiments, α2M was purchased from SIGMA. BALB/c mice were obtained from Jackson Labs (Bar Harbor, Me.) and used at 6-8 weeks of age.

In order to test if immunogenic α2M complexes can be used as a prophylaxis against tumor formation, groups of naïve mice, consisting of 5 mice per group, unless otherwise stated, were immunized with 7 µg of isolated α2M complexes. All immunizations were performed intradermally in 100 µl PBS.

The sources of α2M antigenic molecule complexes for immunizations included: 1) serum of mice bearing 2 cm intradermal MethA tumor; 2) serum of mice 24 hrs after injecting 50% bleach directly into the 2 cm tumor (15 mice); 3) serum of mice with ascites that was induced by interperitoneal injection of live tumor cells (15 mice); 4) serum of non-tumor bearing mice, as a negative control; 5) serum of mice immunized with α2M complexed to Meth A10 (peptides<10 kDa derived from MethA tumor lysate), as such complexes were previously shown to protect against a challenge with MethA tumor cells (Binder, 2002, Cancer Immunity, supra); 6) serum of mice immunized with gp96 complexed to MethA10, as a positive control, called gp96-MethA10, as it was also previously shown to protect against a challenge with MethA tumor cells (Binder, 2002, Cancer Immunity, supra); 7) serum of mice immunized with PBS, as a negative control, called PBS1: 8) serum of mice immunized with PBS as a negative control, called PBS2; 9) serum of mice immunized with liver-derived gp96 as a negative control; 10) serum of mice immunized with MethA-derived gp96, as a positive control, since gp96 was known to complex with antigenic molecules and stimulate immunity (Srivastava et al., 1986, supra); and 11) serum of mice immunized with whole irradiated MethA tumor cells to determine if such cells could provide protection as a positive control.

Animals were then challenged intradermally with 100,000 live tumor cells one week after the last immunization. Tumors were measured in two dimensions. Half of the average was used as the radius of the tumor to calculate the tumor volume (mm$^3$). Observations were made and values recorded at day 7, 9, 12, 15, and 18.

Results

The results of the immunizations are shown in FIG. 1 and Table 2. The negative control groups of mice PBS1, and PBS2 indicate no cessation or reduction in tumor development, whereas animals that had been immunized with alpha (2) macroglobulin complexes from tumor-bearing animals exhibited a decline in tumor development by day 12. By day 15, dramatic differences are evident in tumor volume between the control groups and animals immunized with alpha (2) macroglobulin complexes derived from tumor-bearing animals. Complexes isolated from serum of tumor-bearing animals or from serum of mice with ascites were both effective at preventing tumor growth in challenged mice. Complexes isolated from tumor-bearing mice that had bleach injected into the tumors to induce tumor necrosis exhibited particularly effective protection, with no tumor volume beyond 280 mm$^3$ observed. Alpha (2) macroglobulin complexes derived from the serum of a mice bearing intradermal tumors were also found to more effectively inhibit tumor growth than complexes derived from serum of mice with ascites.

Alpha (2) macroglobulin from normal mice had no effect or minimal protective effect.

TABLE 2

| | 0 | 7 | 9 | 12 | 15 | 18 |
|---|---|---|---|---|---|---|
| PBS | | | | | | |
| 1 | 0 | 120.25 | 117.62 | 314.63 | 687.10 | 715.73 |
| 2 | 0 | 43.23 | 44.43 | 185.34 | 263.95 | 881.90 |
| 3 | 0 | 64.83 | 181.43 | 167.47 | 372.05 | 696.56 |
| 4 | 0 | 204.84 | 81.27 | 733.28 | 764.17 | 927.17 |
| 5 | 0 | 48.01 | 46.74 | 230 | 820.04 | 1136.55 |
| Whole Cells | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| A2M Ascites 1 | | | | | | |
| 1 | 0 | 249.31 | 328.82 | 0 | 0 | 0 |
| 2 | 0 | 32.251 | 327.10 | 349.99 | 369.56 | 641.11 |
| 3 | 0 | 194.52 | 303.58 | 0 | 0 | 0 |
| 4 | 0 | 201.92 | 183.38 | 199.84 | 353.61 | 492.56 |
| 5 | 0 | 140.10 | 156.70 | 0 | 0 | 0 |
| A2M Ascites 2 | | | | | | |
| 1 | 0 | 130.55 | 232.92 | 209.93 | 243.60 | 387.90 |
| 2 | 0 | 331.13 | 237.53 | 0 | 0 | 0 |
| 3 | 0 | 95.65 | 102.90 | 464.46 | 950.29 | 1217.38 |
| 4 | 0 | 108.85 | 83.56 | 0 | 0 | 0 |
| 5 | 0 | 91.17 | 128.38 | 132.42 | 234.29 | 350.59 |
| A2M Ascites 3 | | | | | | |
| 1 | 0 | 19.76 | 231.09 | 160.95 | 293.33 | 407.51 |
| 2 | 0 | 98.46 | 130.55 | 180.275 | 60.63 | 143.72 |
| 3 | 0 | 139.78 | 115.32 | 0 | 0 | 0 |
| 4 | 0 | 139.13 | 253.64 | 0 | 0 | 0 |
| A2M Bleach 1 | | | | | | |
| 1 | 0 | 106.66 | 209.07 | 56.80 | 65.02 | 118.79 |
| 2 | 0 | 104.77 | 67.60 | 0 | 0 | 0 |
| 3 | 0 | 64.44 | 87.78 | 25.89 | 0 | 0 |
| 4 | 0 | 217.27 | 211.64 | 0 | 0 | 0 |
| 5 | 0 | 134.00 | 216.39 | 0 | 0 | 0 |

TABLE 2-continued

| | 0 | 7 | 9 | 12 | 15 | 18 |
|---|---|---|---|---|---|---|
| A2M Bleach 2 | | | | | | |
| 1 | 0 | 172.29 | 149.43 | 0 | 0 | 0 |
| 2 | 0 | 192.90 | 185.34 | 0 | 0 | 0 |
| 3 | 0 | 157.75 | 280.19 | 0 | 0 | 0 |
| 4 | 0 | 177.21 | 270.97 | 0 | 0 | 0 |
| 5 | 0 | 86.12 | 301.95 | 0 | 0 | 0 |
| A2M Bleach 3 | | | | | | |
| 1 | 0 | 24.72 | 82.86 | 180.27 | 0 | 0 |
| 2 | 0 | 6.97 | 0 | 0 | 0 | 0 |
| 3 | 0 | 60.26 | 42.05 | 0 | 0 | 0 |
| 4 | 0 | 4.38 | 7.70 | 0 | 0 | 0 |
| A2M Tumor-Bearing 1 | | | | | | |
| 1 | 0 | 132.42 | 136.23 | 0 | 0 | 0 |
| 2 | 0 | 144.72 | 184.94 | 0 | 0 | 0 |
| 3 | 0 | 243.60 | 285.39 | 0 | 0 | 0 |
| 4 | 0 | 3.052 | 93.89 | 0 | 0 | 0 |
| 5 | 0 | 117.33 | 128.69 | 0 | 0 | 0 |
| A2M Non-Tumor Bearing | | | | | | |
| 1 | 0 | 149.09 | 255.58 | 331.71 | 507.79 | 605.82 |
| 2 | 0 | 103.17 | 73.37 | 65.42 | 0 | 0 |
| 3 | 0 | 123.22 | 203.17 | 346.40 | 527.27 | 605.82 |
| 4 | 0 | 117.62 | 297.08 | 119.96 | 158.11 | 220.78 |
| 5 | 0 | 101.84 | 129.31 | 249.78 | 382.78 | 448.69 |
| Gp96 isolated from Meth A tumor cells | | | | | | |
| 1 | 0 | 179.50 | 140.43 | 0 | 0 | 0 |
| 2 | 0 | 128.69 | 256.56 | 0 | 0 | 0 |
| 3 | 0 | 190.09 | 125.94 | 0 | 0 | 0 |
| 4 | 0 | 0 | 127.46 | 0 | 0 | 0 |
| 5 | 0 | 148.08 | 91.66 | 85.65 | 350.59 | 523.33 |
| 10 kDa peptide complexed to A2M | | | | | | |
| 1 | 0 | 79.91 | 98.20 | 29.06 | 0 | 0 |
| 2 | 0 | 26.40 | 117.04 | 0 | 0 | 0 |
| 3 | 0 | 170.43 | 276.07 | 0 | 0 | 0 |
| 4 | 0 | 174.17 | 266.447 | 0 | 0 | 0 |
| 5 | 0 | 97.43 | 220.79 | 0 | 0 | 0 |
| gp96 complexes isolated from normal liver | | | | | | |
| 1 | 0 | 96.41 | 180.27 | 399.59 | 528.85 | 795.92 |
| 2 | 0 | 137.19 | 274.02 | 318.56 | 650.14 | 795.92 |
| 3 | 0 | 150.80 | 235.68 | 327.67 | 503.19 | 696.56 |
| 4 | 0 | 142.40 | 124.12 | 305.77 | 650.14 | 1022.14 |
| 5 | 0 | 140.76 | 348.79 | 651.04 | 893.06 | 1149.76 |
| 10 kDa peptide complexed to gp96 | | | | | | |
| 1 | 0 | 150.45 | 168.21 | 0 | 0 | 0 |
| 2 | 0 | 223.44 | 312.96 | 0 | 0 | 0 |
| 3 | 0 | 95.14 | 173.42 | 0 | 0 | 0 |
| 4 | 0 | 212.07 | 138.16 | 0 | 0 | 0 |
| 5 | 0 | 145.39 | 84.72 | 0 | 0 | 0 |
| PBS 2 | | | | | | |
| 1 | 0 | 213.36 | 227.47 | 175.31 | 305.22 | 605.82 |
| 2 | 0 | 157.05 | 44.43 | 362.75 | 550.48 | 696.56 |
| 3 | 0 | 19.15 | 181.43 | 317.44 | 881.90 | 1022.14 |
| 4 | 0 | 146.39 | 81.27 | 379.61 | 428.46 | 605.82 |
| 5 | 0 | 73.16 | 46.74 | 229.73 | 806.35 | 1149.76 |

Conclusion

The results of the experiments indicate that alpha (2) macroglobulin complexes can be administered to effectively treat or prevent cancer. The decrease in tumor volume demonstrates an effective treatment method. The prophylactic effects of administering complexes to animals later challenged with tumor cells is evident. The degree of effectiveness observed in animals administered complexes derived from an animal that had first been treated with bleach, which caused necrosis of tumor cells, is particularly unexpected and promising. The necrosis of tumor cells facilitates shedding of antigenic molecules specific to the tumor which then complex with alpha (2) macroglobulin in bodily The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein, including patent applications, patents, and other publications, are incorporated by reference herein in their entireties for all purposes.

What is claimed is:

1. A method for preparing purified alpha (2) macroglobulin-antigenic molecule complexes comprising (a) purifying endogenous alpha (2) macroglobulin-antigenic molecule complexes from serum from a patient having a cancerous tumor or an infectious disease, wherein said complexes comprise an antigenic molecule having the antigenicity of said cancerous tumor or an infectious agent of said infectious disease, respectively, wherein said complexes when purified from said patient having said cancerous tumor, are in an amount effective to treat said cancerous tumor, and wherein said complexes when purified from said patient having said infectious disease, are in an amount effective to treat said infectious disease; and (b) formulating the purified alpha (2) macroglobulin-antigenic molecule complexes in a compatible pharmaceutical carrier.

2. The method of claim 1, wherein said patient has said cancerous tumor, and wherein the method further comprises a step of administering to said patient said amount of the purified complexes effective to treat said cancerous tumor.

3. The method of claim 1 wherein in the step of purifying alpha (2) macroglobulin-antigenic molecule complexes from said serum comprises:
   (a) contacting a solid phase containing an alpha (2) macroglobulin-binding molecule with the serum for a time period sufficient to allow binding of the alpha (2) macroglobulin-antigenic molecule complexes with the solid phase;
   (b) removing material not bound to the solid phase; and
   (c) eluting the bound alpha (2) macroglobulin-antigenic molecule complexes from the solid phase.

4. The method of claim 3 wherein the alpha (2) macroglobulin-binding molecule is an antibody specific to alpha (2) macroglobulin.

5. The method of claim 3 wherein the alpha (2) macroglobulin-binding molecule is a ligand-binding fragment of CD91.

6. The method of claim 1 wherein said purifying step comprises fractionating the serum to enrich for alpha (2) macroglobulin-antigenic molecule complexes.

7. The method of claim 1 or 6 further comprising the step of contacting the serum with an agent which stimulates covalent bond formation between the alpha (2) macroglobulin and the antigenic molecules.

8. The method of claim 7 wherein the agent which stimulates covalent bond formation is a protease, ammonia, methylamine or ethylamine.

9. The method of claim 6 wherein said purifying step subsequent to fractionating the serum further comprises:
   (a) determining alpha (2) macroglobulin-positive fractions;
   (b) applying the alpha (2) macroglobulin-positive fractions to a Concanavalin A sepharose column; and
   (c) eluting bound complexes.

10. The method of claim 1, 2, or 6, wherein the patient is a human.

11. The method of claim 1 or 6, wherein the compatible pharmaceutical carrier is a physiologically compatible solution.

12. The method of claim 1, wherein said patient has said cancerous tumor, and wherein said complexes comprise an antigenic molecule having the antigenicity of said cancerous tumor.

13. The method of claim 12, wherein the patient is a human.

14. The method of claim 1, wherein said patient has said infectious disease, and wherein the method further the comprises a step of administering to said patient said amount of the purified complexes effective to treat said infectious disease.

15. The method of claim 14, wherein the patient is a human.

* * * * *

UNITED STATES PATENT AND TRADEMARK OFFICE
CERTIFICATE OF CORRECTION

| | | |
|---|---|---|
| PATENT NO. | : 8,877,204 B2 | Page 1 of 1 |
| APPLICATION NO. | : 10/546106 | |
| DATED | : November 4, 2014 | |
| INVENTOR(S) | : Pramod K. Srivastava et al. | |

It is certified that error appears in the above-identified patent and that said Letters Patent is hereby corrected as shown below:

In the Claims:
At column 54, lines 36-37, claim 14, "infectious disease, and wherein the method further the comprises" should read --infectious disease, and wherein the method further comprises--

Signed and Sealed this
Seventeenth Day of February, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,877,204 B2  
APPLICATION NO. : 10/546106  
DATED : November 4, 2014  
INVENTOR(S) : Srivastava et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,616 days.

Signed and Sealed this
Eighteenth Day of April, 2017

Michelle K. Lee
*Director of the United States Patent and Trademark Office*